United States Patent
Victor et al.

(10) Patent No.: US 8,901,282 B2
(45) Date of Patent: Dec. 2, 2014

(54) REAGENTS AND METHODS FOR DETECTING A POLYMORPHIC PROTEIN

(75) Inventors: Jacob Victor, Passaic, NJ (US); Noah Berkowitz, New Rochelle, NY (US); Andrew Levy, Haifa (IL)

(73) Assignee: Rappaport Family Institute for Research in the Medical Sciences, Haifa (IL)

( * ) Notice: Subject to any disclaimer, the term of this patent is extended or adjusted under 35 U.S.C. 154(b) by 986 days.

(21) Appl. No.: 12/997,856

(22) PCT Filed: Jun. 11, 2009

(86) PCT No.: PCT/US2009/047024
§ 371 (c)(1),
(2), (4) Date: Aug. 12, 2011

(87) PCT Pub. No.: WO2009/152319
PCT Pub. Date: Dec. 17, 2009

(65) Prior Publication Data
US 2011/0294145 A1    Dec. 1, 2011

Related U.S. Application Data

(60) Provisional application No. 61/129,250, filed on Jun. 13, 2008.

(51) Int. Cl.
*C07K 16/00* (2006.01)
*G01N 33/68* (2006.01)
*C07K 16/18* (2006.01)

(52) U.S. Cl.
CPC ............ *C07K 16/18* (2013.01); *G01N 33/6893* (2013.01); *C07K 2317/56* (2013.01); *C07K 2317/92* (2013.01); *G01N 2800/042* (2013.01)
USPC ................ 530/388.25; 530/388.1; 530/388.2; 530/387.1; 435/7.92

(58) Field of Classification Search
None
See application file for complete search history.

(56) References Cited

U.S. PATENT DOCUMENTS

| | | |
|---|---|---|
| 6,251,608 B1 | 6/2001 | Levy |
| 6,599,702 B1 | 7/2003 | Levy |
| 6,613,519 B1 | 9/2003 | Levy |
| 6,632,926 B1 | 10/2003 | Chen |
| 6,750,325 B1 | 6/2004 | Jolliffe |
| 7,608,393 B2 | 10/2009 | Levy |
| 2003/0138862 A1 | 7/2003 | Tso |
| 2003/0233675 A1 | 12/2003 | Cao |
| 2004/0101904 A1 | 5/2004 | Pardridge |
| 2004/0123343 A1 | 6/2004 | La Rosa |
| 2005/0220793 A1 | 10/2005 | Anderson |
| 2006/0014138 A1 | 1/2006 | Chinnaiyan |
| 2006/0165686 A1 | 7/2006 | Elson |
| 2006/0228753 A1* | 10/2006 | Levy et al. ..................... 435/7.1 |
| 2009/0074740 A1 | 3/2009 | Berkowitz |
| 2011/0288013 A1 | 11/2011 | Levy |
| 2011/0301186 A1 | 12/2011 | Levy |

FOREIGN PATENT DOCUMENTS

| | | |
|---|---|---|
| WO | 2005/062706 A2 | 7/2005 |
| WO | 2006/076691 A2 | 7/2006 |
| WO | 2012/160559 A1 | 11/2012 |

OTHER PUBLICATIONS

Ball R. K. et al., (1983) The complete amino acid sequence of the light chain variable region of two monoclonal anti-p-azobenzene-arsonate antibodies bearing the cross-reactive idiotype. Mol Immunol 20(2): 197-201.
Chothia C. et al., (1985) Domain association in immunoglobulin molecules. The packing of variable domains. J Mol Biol 186(3): 651-63.
Costecou T. et al., (2008) Haptoglobin genotype: a determinant of cardiovascular complication risk in Type 1 diabetes. Diabetes 57(6): 1702-6.
Holliger P. et al., (1993) "Diabodies": small bivalent and bispecific antibody fragments. Proc Natl Acad Sci USA 90 (14): 6444-8.
Langlois M. and Delanghe J. (1996) Biological and clinical significance of haptoglobin polymorphism in humans. Clin Chem 42(10): 1589-1600.
Levy A. P. et al, (2000) Haptoglobin phenotype and vascular complications in patients with diabetes. New Eng J Med 343(13): 969-70.
Levy A. P. et al, (2002) Haptoglobin phenotype is an independent risk factor for cardiovascular disease in individuals with diabetes: The Strong Heart Study. J Am Coll Cardiol 40(11): 1984-90.
Levy N. S. et al., (2013) An enzyme linked immunosorbent assay (ELISA) for the determination of the human haptoglobin phenotype. Clin Chem Lab Med 51(8): 1615-22.
Morrison S. L. et al., (1984) Chimeric human antibody molecules: mouse antigen-binding domains with human constant region domains. Proc Natl Acad Sci USA 81(21): 6851-5.
Novotny J. and Haber E. (1985) Structural invariants of antigen binding: comparison of immunoglobulin VL-VH and VL-VL domain dimers. Proc Natl Acad Sci USA. 82(14): 4592-6.
Riechmann L. et al., (1988) Reshaping human antibodies for therapy. Nature 332(6162): 323-7.
Worn A. and Pluckthun A. (2001) Stability engineering of antibody single-chain Fv fragments. J Mol Biol 305(5): 989-1010.
B0WH76_CULQU. UniProt (online) (May 20, 2008) [retrieved on Oct. 8, 2009] retrieved from the internet URL:<http://www.uniprot.org/uniprot/B0WH76.txt?version=2>. see amino acid sequence.

* cited by examiner

*Primary Examiner* — Galina Yakovleva
*Assistant Examiner* — Andrea S Grossman
(74) *Attorney, Agent, or Firm* — Pearl Cohen Zedek Latzer Baratz LLP

(57) ABSTRACT

The present invention provides antibodies that differentially react with allelic variants of a polymorphic protein, methods of identifying same, an antigen binding fragment comprised therein, proteins, cells, viral particles, compositions, and kits comprising same. The invention also provides methods for determining a haptoglobin type of a subject and methods for testing a subject for susceptibility to diabetic complications.

12 Claims, No Drawings

SEQUENCE LISTING

<160> NUMBER OF SEQ ID NOS: 10

<210> SEQ ID NO 1
<211> LENGTH: 409
<212> TYPE: DNA
<213> ORGANISM: Mouse

<400> SEQUENCE: 1

```
agcctggaca tgatgtcctc tgctcagttc cttggtctcc tgttgctctg ttttcaaggt      60
agcagatgtg atatccagat gacacagact acatcctccc tgtctgcctc tctgggagac     120
agagtcacca tcagttgcag ggcaagtcag gacattagga aatatttaaa ctggtatcag     180
cagaaaccag atggaactgt taaactcctg atctactaca catcaagatt atattcggca     240
gtcccatcaa ggttcagtgg cagtgggtct ggaacagatt attctctcac cattagcaac     300
ctggaacaag aagatattgc catgtacttt tgtcaacaga gtgataggct tccttacacg     360
ttcggagggg ggaccaagct ggaaatcaaa cgtaagtcga ctgcaccaa               409
```

<210> SEQ ID NO 2
<211> LENGTH: 134
<212> TYPE: PRT
<213> ORGANISM: Mouse

<400> SEQUENCE: 2

```
Ser Leu Asp Met Met Ser Ser Ala Gln Phe Leu Gly Leu Leu Leu Leu
 1               5                  10                  15

Cys Phe Gln Gly Ser Arg Cys Asp Ile Gln Met Thr Gln Thr Thr Ser
             20                  25                  30

Ser Leu Ser Ala Ser Leu Gly Asp Arg Val Thr Ile Ser Cys Arg Ala
         35                  40                  45

Ser Gln Asp Ile Arg Lys Tyr Leu Asn Trp Tyr Gln Gln Lys Pro Asp
     50                  55                  60

Gly Thr Val Lys Leu Leu Ile Tyr Tyr Thr Ser Arg Leu Tyr Ser Ala
 65                  70                  75                  80

Val Pro Ser Arg Phe Ser Gly Ser Gly Ser Gly Thr Asp Tyr Ser Leu
                 85                  90                  95

Thr Ile Ser Asn Leu Glu Gln Glu Asp Ile Ala Met Tyr Phe Cys Gln
            100                 105                 110

Gln Ser Asp Arg Leu Pro Tyr Thr Phe Gly Gly Gly Thr Lys Leu Lys
        115                 120                 125

Arg Lys Ser Thr Ala Pro
    130
```

<210> SEQ ID NO 3
<211> LENGTH: 15
<212> TYPE: PRT
<213> ORGANISM: Mouse

<400> SEQUENCE: 3

```
Cys Asp Arg Leu Arg Ala Ser Gln Asp Ile Arg Lys Tyr Leu Asn
 1               5                  10                  15
```

<210> SEQ ID NO 4
<211> LENGTH: 11
<212> TYPE: PRT
<213> ORGANISM: Mouse

<400> SEQUENCE: 4

```
Cys Asp Arg Leu Tyr Thr Ser Arg Leu Tyr Ser
 1               5                  10
```

<210> SEQ ID NO 5
<211> LENGTH: 13
<212> TYPE: PRT
<213> ORGANISM: Mouse

-continued

<400> SEQUENCE: 5

Cys Asp Arg Leu Gln Gln Ser Asp Arg Leu Pro Tyr Thr
1               5                   10

<210> SEQ ID NO 6
<211> LENGTH: 456
<212> TYPE: DNA
<213> ORGANISM: Mouse

<400> SEQUENCE: 6

```
tggccaatgt cctctccaca gtccctgaag acactgattc taaccatggg atggagctgg      60
atctttctct tcctcctgtc aggaactgca ggtgtccact cccaggttca gctgcagcag     120
tctggacctg agctggtgaa gcctggggct tcagtgaagt tgtcctgcaa ggcttctggc     180
tacaccttca aagttatga tataaactgg gtgaagcaga ggcctggaca gggacttgag     240
tggattggtt ggatttatcc tagagatggt agtactaaat acaatgcgaa cttcaagggc     300
agggccacat tgactgtgga cacctcctcc agcacagtgt atatggaaat ccacagcctg     360
acatctgagg actctgcggt ctatttctgt gcaagagacc ccgattacta cggtagtgtt     420
gactattggg gccaaggcac cactctcacc gtctct                                456
```

<210> SEQ ID NO 7
<211> LENGTH: 150
<212> TYPE: PRT
<213> ORGANISM: Mouse

<400> SEQUENCE: 7

Trp Pro Met Ser Ser Pro Gln Ser Leu Lys Thr Leu Ile Leu Thr Met
1               5                   10                  15

Gly Trp Ser Trp Ile Phe Leu Phe Leu Leu Ser Gly Thr Ala Gly Val
                20                  25                  30

His Ser Gln Val Gln Leu Gln Gln Ser Gly Pro Glu Leu Val Lys Pro
            35                  40                  45

Gly Ala Ser Val Lys Leu Ser Cys Lys Ala Ser Gly Tyr Thr Phe Ile
        50                  55                  60

Ser Tyr Asp Ile Asn Trp Val Lys Gln Arg Pro Gly Gln Gly Leu Glu
65                  70                  75                  80

Trp Ile Gly Trp Ile Tyr Pro Arg Asp Gly Ser Thr Lys Tyr Asn Ala
                85                  90                  95

Asn Phe Lys Gly Arg Ala Thr Leu Thr Val Asp Thr Ser Ser Ser Thr
            100                 105                 110

Val Tyr Met Glu Ile His Ser Leu Thr Ser Glu Asp Ser Ala Val Cys
        115                 120                 125

Ala Arg Asp Pro Asp Tyr Tyr Gly Ser Val Asp Tyr Trp Gly Gln Gly
    130                 135                 140

Thr Thr Leu Thr Val Ser
145             150

<210> SEQ ID NO 8
<211> LENGTH: 14
<212> TYPE: PRT
<213> ORGANISM: Mousw

<400> SEQUENCE: 8

Cys Asp Arg His Gly Tyr Thr Phe Ile Ser Tyr Asp Ile Asn
1               5                   10

```
<210> SEQ ID NO 9
<211> LENGTH: 21
<212> TYPE: PRT
<213> ORGANISM: Mouse

<400> SEQUENCE: 9

Cys Asp Arg His Trp Ile Tyr Pro Arg Asp Gly Ser Thr Lys Tyr Asn
1               5                   10                  15

Ala Asn Phe Lys Gly
            20

<210> SEQ ID NO 10
<211> LENGTH: 14
<212> TYPE: PRT
<213> ORGANISM: Mouse

<400> SEQUENCE: 10

Cys Asp Arg His Asp Pro Asp Tyr Tyr Gly Ser Val Asp Tyr
1               5                   10
```

REAGENTS AND METHODS FOR DETECTING A POLYMORPHIC PROTEIN

CROSS-REFERENCE TO RELATED APPLICATIONS

This application is a National Phase Application of PCT International Application No. PCT/US09/47024, International Filing Date Jun. 11, 2009, claiming priority of U.S. Provisional Patent Application No. 61/129,250, filed Jun. 13, 2008, of which are incorporated herein by reference in their entirety.

FIELD OF THE INVENTION

The present invention provides antibodies that differentially react with allelic variants and isoforms of a polymorphic protein, methods of identifying same, an antigen binding fragment comprised therein, proteins, cells, viral particles, compositions, and kits comprising same. The invention also provides methods for determining a haptoglobin type of a subject and methods for testing a subject for susceptibility to diabetic complications among other risk factors.

BACKGROUND OF THE INVENTION

The haptoglobin genetic locus at 16q22 is polymorphic with two known classes of alleles denoted 1 and 2 (Langlois M et al, Clin Chem 42: 1589-1600, 1996). The polymorphism is quite common, with worldwide frequencies of the two alleles being approximately equal. Haptoglobin is a major susceptibility gene for the development of diabetic vascular complications in multiple longitudinal and cross-sectional population studies (Levy A et al, New Eng J Med 343: 969-70, 2000; Roguin A et al, Am J Cardiol 87: 330-2, 2001). Diabetic individuals homozygous for the haptoglobin 2 (Hp 2) allele are at 5 times greater risk of developing cardiovascular disease as compared to diabetic individuals homozygous for the haptoglobin 1 allele (Hp 1), with an intermediate risk present in the heterozygote (Levy A et al, J Am Coll Cardiol 40: 1984-90, 2002). The risk pertains to both type 1 and type 2 diabetes (Costecou, T. Ferrell, R E, Orchard T J. Haptoglobin genotype: a determinant of cardiovascular complication risk in Type 1 diabetes. Diabetes 57:1702-1706 (2008)). Mechanistic studies using the purified protein products of the Hp 1 and Hp 2 alleles have identified profound differences in antioxidant and immunomodulatory activity (Frank M et al, Blood; 98: 3693-8, 2001; Asleh R et al, Circ Res 92: 1193-200, 2003).

Functional as well as structural differences exist between the various haptoglobin allelic protein products (Langlois M et al, Clin Chem 42: 1589-1600, 1996). The Hp 2 allele has two copies of exon 3 and 4 of the Hp1 allele, which results in the duplication of a multimerization domain in exon 3. Consequently, while the Hp1 allele protein product forms only dimers, Hp2 allele protein products combine to form cyclic polymers ranging in size from three monomers and upwards. In heterozygotes, linear polymers containing both allelic protein products are present.

The development of an antibody based ELISA test to type haptoglobin has been hampered by the apparent lack of antigenic determinants unique to either allelic protein product. Apart from a single junction at the site of duplication of exon three, there exist no differences in primary amino acid sequence between the haptoglobin alleles. Given the need to screen large populations of diabetic individuals (10% of the western world) for their haptoglobin type in order to determine optimal treatment as well as the need to screen certain populations rapidly (i.e. individuals suffering from an acute myocardial infarction) there is a great need for a simple, rapid, inexpensive test for haptoglobin phenotyping.

SUMMARY OF THE INVENTION

In one embodiment, the present invention provides an antibody or an antigen-binding fragment thereof of an anti-haptoglobin (Hp) antibody that binds with greater affinity to a first haptoglobin isoform than to a second haptoglobin isoform. In another embodiment, the anti-haptoglobin (Hp) antibody or antigen-binding fragment thereof binds with greater affinity to Hp 2-2 than to Hp 2-1, and with greater affinity to Hp 2-1 than to Hp 1-1. In another embodiment the haptoglobin isoforms are human. In another embodiment, the antibody or antigen-binding fragment thereof is monoclonal antibody designated 1E10, 1G1, 2B3, 3H3, 4F9, 4G12, 4D3, and 4D6.

In another embodiment, the anti-haptoglobin monoclonal antibody is that produced by the murine hybridoma deposited with the ATCC with a patent deposit designation PTA-9815. In another embodiment, a composition of the aforementioned antibody or an antigen-binding fragment thereof is provided.

In other embodiments, the antibodies may be humanized or chimeric. In another embodiment, the antibody may be an scFv antibody.

In another embodiment, compositions are provided comprising a cell, a packaging cell line, an antibody, a recombinant protein, or a recombinant viral particle comprising any anti-haptoglobin antibody described herein or an antigen binding fragment thereof.

In yet another embodiment, a complementarity-determining region of an anti-haptoglobin antibody as embodied herein is provided that binds with greater affinity to a first haptoglobin isoform than to a second haptoglobin isoform. In one embodiment, the complementarity-determining region binds with greater affinity to haptoglobin isoform Hp 2-2 than to Hp 2-1. In another embodiment, the complementarity-determining region binds with greater affinity to haptoglobin isoform Hp 2-1 than to Hp 1-1. In another embodiment, the complementarity-determining region binds with greater affinity to haptoglobin isoform Hp 2-2 than to Hp 1-1. In another embodiment the haptoglobin isoforms are human.

In another embodiment, a monoclonal antibody or an antigen-binding portion thereof is provided having a binding affinity in decreasing order to the Hp 2-2; Hp 2-1; and Hp 1-1 is forms of haptoglobin, wherein the light chain variable region of said antibody comprises the light chain complementarity determining region (CDRL) 1, the CDRL2 and the CRDL3 from an antibody selected from the group consisting of 1E10, 1G1, 2B3, 3H3, 4F9, 4G12, 4D3, 4D6 or the murine hybridoma deposited with the ATCC with a patent deposit designation PTA-9815; and the heavy chain variable region of said antibody comprises heavy chain complementarity determining region (CDRH) 1, CDRH2 and CDRH3 from said an antibody selected from the group consisting of 1E10, 1G1, 2B3, 3H3, 4F9, 4G12, 4D3, 4D6 or the murine hybridoma deposited with the ATCC with a patent deposit designation PTA-9815. In another embodiment the haptoglobin isoforms are human.

In another embodiment, a monoclonal anti-haptoglobin monoclonal antibody is provided that comprises at least one light chain variable region and at least one heavy chain variable region, said light chain variable region comprising: a CDRL1 having amino acid sequence SEQ ID NO:3; a CDRL2 having amino acid sequence SEQ ID NO:4; and a CDRL3 having amino acid sequence of SEQ ID NO:5, and said heavy chain variable region comprising: a CDRH1 having amino acid sequence SEQ ID NO:8; a CDRH2 having amino acid sequence SEQ ID NO:9; and a CDRH3 having amino acid sequence SEQ ID NO:10.

In another embodiment, the aforementioned antibody comprises a light chain variable region amino acid sequence of SEQ ID NO:2. In another embodiment, the aforementioned antibody comprises a heavy chain variable region amino acid sequence of SEQ ID NO:7. And in another embodiment, the monoclonal antibody comprises the light chain variable region amino acid sequence SEQ ID NO:2 and a heavy chain variable amino acid sequence of SEQ ID NO:7.

In other embodiment, any of the aforementioned antibodies can have a light or heavy chain variable region that is at least one of chimerized, humanized, or CDR-grafted.

In another embodiment, any of the aforementioned anti-haptoglobin antibodies can further comprise at least one compound or polypeptide selected from a detectable label or reporter. By way of non-limiting example, the detectable label is an enzyme such as horseradish peroxidase or alkaline phosphatase.

In another embodiment, the present invention provides an isolated nucleic acid encoding any anti-haptoglobin (Hp) antibody of the present invention. In another embodiment, the antibodies are monoclonal antibodies designated 1E10, 1G1, 2B3, 3H3, 4F9, 4G12, 4D3, 4D6 or the murine hybridoma deposited with the ATCC with a patent deposit designation PTA-9815. In a further embodiment, host cells are provided that produce the aforementioned monoclonal antibodies.

In a further embodiment, antibodies are provided that have a light chain variable region encoded by a nucleotide sequence of SEQ ID NO: 1. In another embodiment, antibodies re provided that have a heavy chain variable sequence encoded by a nucleotide sequence of SEQ ID NO:6. In further embodiments, said nucleotide sequence may encode light and heavy chains with one or more conservatively substituted amino acids.

In another embodiment, a method of determining a haptoglobin phenotype type of a subject is provided, comprising
  a) contacting a biological sample of said subject with an anti-haptoglobin antibody embodied herein or an antigen binding fragment thereof, forming a bound complex between the anti-haptoglobin antibody or fragment and haptoglobin in the biological sample;
  b) quantitatively determining a binding affinity between said haptoglobin and said anti-haptoglobin antibody or fragment; and
  c) comparing said quantitatively determined binding affinity with a value obtained from a quantitatively determined binding affinity of said anti-haptoglobin antibody or antigen binding fragment thereof to an isolated Hp 1-1, Hp 2-1, or Hp 2-2 isoform, wherein the binding affinity determined is indicative of the Hp isoform type, thereby determining the phenotype type of Hp in said subject.

In another embodiment, the biological sample is serum. In a further embodiment the biological sample is plasma. In other embodiments, the plasma is plasma that has been anticoagulated with citrate, heparin or EDTA.

In a further embodiment of the foregoing method, the anti-haptoglobin antibody-antigen complex can be immobilized on a substrate, such as by binding the anti-haptoglobin antibody or antigen-binding fragment thereof to the substrate. In certain embodiments the anti-haptoglobin antibody on the substrate is a polyclonal anti-haptoglobin antibody, and in other embodiments, it can be a monoclonal anti-haptoglobin antibody, such as but not limited to any aforementioned antibody including 1E10, 1G1, 2B3, 3H3, 4F9, 4G12, 4D3, 4D6 or the murine hybridoma deposited with the ATCC with a patent deposit designation PTA-9815.

In further embodiments, the foregoing method can further comprise contacting said immobilized complex with an additional quantity of said anti-haptoglobin antibody or antigen binding fragment thereof; and determining a binding affinity between said antigen and said additional quantity of said anti-haptoglobin antibody or antigen binding fragment thereof.

In further embodiments, said additional anti-haptoglobin antibody can be any of the aforementioned antibodies or an antigen-binding fragment thereof. In other embodiments, the additional antibody can further comprise a detectable label or reporter; the label can be, by way of non-limiting example, an enzyme such as horseradish peroxidase or alkaline phosphatase. In another embodiment the label can be a fluorophore.

In the foregoing methods embodied here, the antibody, recombinant protein or antigen binding fragment thereof can be provided at a dilution below the concentration wherein differential binding affinity among the different haptoglobin isoforms is not observed, such as but not limited to a dilution of 10-1000 times below the concentration wherein differential binding affinity among different haptoglobin isoforms is not observed. In another embodiment the haptoglobin isoforms are human.

In another embodiment, the aforementioned methods provide results in less than about three hours. In another embodiment, results are provided in less than about 1-2 hours. In other embodiments, point-of-care devices facilely utilized in a health practitioner's office or even in the home can provide results in around 10-20 minutes, or even less.

In another embodiment, a method is provided for testing a subject for susceptibility to a diabetic complication, comprising the step of determining the subject's haptoglobin phenotype according to any of the foregoing methods, wherein the presence of the Hp 2-2 phenotype indicates higher susceptibility to a diabetic complication. In some embodiments, the diabetic complication is one or more vascular complication such as but not limited to chronic heart failure, cardiovascular death, stroke, myocardial infarction, coronary angioplasty associated restenosis, diabetic retinopathy, diabetic nephropathy and diabetic neuropathy, fewer coronary artery collateral blood vessels and myocardial ischemia.

In another embodiment, a method is provided for testing a diabetic subject for a potential to benefit from reducing oxidative stress or anti-oxidant therapy and thereby reducing the risk or incidence of vascular disease, comprising the step of determining the subject's haptoglobin phenotype according to any of the foregoing methods, wherein the presence of Hp 2-2 indicates a greater benefit of reducing oxidative stress or anti-oxidant therapy and thereby reducing the risk or incidence of vascular disease. In another embodiment, the vascular disease is chronic heart failure, cardiovascular death, stroke, myocardial infarction, coronary angioplasty associated restenosis, diabetic retinopathy, diabetic nephropathy and diabetic neuropathy, fewer coronary artery collateral blood vessels, myocardial ischemia or any combination thereof. In other embodiments, the reducing oxidative stress is achieved by anti-oxidant therapy. In another embodiment, the anti-oxidant therapy is administration of a vitamin E or an analog, metabolite or derivative thereof.

In further embodiments, a method is provided for testing a candidate antibody a recombinant protein, or an antigen binding fragment thereof for a utility in distinguishing between haptoglobin allele types Hp 1-1, Hp 2-1, or Hp 2-2, comprising the steps of:

a) contacting the candidate antibody, recombinant protein or an antigen binding fragment thereof with a known concentration of isolated Hp 1-1 molecule, Hp 2-1 molecule and Hp 2-2 molecule, forming a complex; and b) quantitatively determining a binding affinity between said candidate antibody, recombinant protein or antigen binding fragment thereof and said Hp 1-1, Hp 2-1, and Hp 2-2; whereby a significantly different binding affinity to each of Hp 1-1, Hp 2-1, and Hp 2-2 indicates that said candidate antibody or recombinant protein is capable of distinguishing between Hp 1-1, Hp 2-1, and Hp 2-2.

In a further embodiment of the foraging method, the complex of said Hp 1-1, Hp 2-1, or Hp 2-2 and said candidate antibody, recombinant protein or antigen binding fragment thereof can be immobilized on a substrate. In another embodiment, the complex can be contacted with an additional quantity of an anti-haptoglobin antibody, recombinant protein or antigen binding fragment thereof subsequent to said immobilizing; and then determining a binding affinity between said Hp 1-1, Hp 2-1, or Hp 2-2 and said additional quantity of said antibody or recombinant protein. In a further embodiment, at least one of the candidate antibody or the additional antibody is the candidate antibody, the other antibody if present can be any of those described herein. In other embodiments, the additional antibody can further comprise a detectable label or reporter; the label can be, by way of non-limiting example, an enzyme such as horseradish peroxidase or alkaline phosphatase. In other embodiments the label is a fluorophore. In another embodiment the haptoglobin isoforms are human.

In a further embodiment, the candidate antibody, recombinant protein or antigen binding fragment thereof can provided at a dilution below the concentration wherein differential binding affinity is not observed, such as but not limited to a dilution of 10-1000 times below the concentration wherein differential binding is not observed.

In another embodiment, a method of testing an antibody or a recombinant protein for a utility in distinguishing between allelic variants of a polymorphic protein is provided, comprising the steps of:

a) contacting the antibody, recombinant protein or an antigen binding fragment thereof with a known concentration of isolated allelic variants of a polymorphic protein; and b) quantitatively determining a binding affinity between said antibody, recombinant protein or antigen binding fragment thereof and said allelic variants; whereby a significantly different binding affinity to each of allelic variants indicates that said antibody or recombinant protein is capable of distinguishing there between.

In a further embodiment, the complex of said allelic variants and said antibody, recombinant protein or antigen binding fragment thereof can be immobilized to a substrate. In a further embodiment, the complex can be contacted with an additional quantity of said antibody, recombinant protein or antigen binding fragment thereof subsequent to said immobilizing; followed by determining a binding affinity between said allelic variants and said additional quantity of said antibody or recombinant protein. In other embodiments, the additional antibody can further comprise a detectable label or reporter; the label can be, by way of non-limiting example, an enzyme such as horseradish peroxidase or alkaline phosphatase.

In further embodiments of the foregoing method, the antibody, recombinant protein or antigen binding fragment thereof is provided at a dilution below the concentration wherein differential binding affinity is not observed. In another embodiment, the dilution is 10-1000 times below the concentration wherein the differential binding affinity is not observed.

In another embodiment, a method is provided for testing a diabetic subject for a potential to benefit from reducing oxidative stress or anti-oxidant therapy and thereby reducing the incidence of cardiovascular disease, comprising the step of determining the subject's haptoglobin phenotype according to any of the foregoing methods, wherein the presence of Hp 2-2 indicates a greater benefit of reducing oxidative stress or anti-oxidant therapy and thereby reducing the incidence of cardiovascular complications. In another embodiment, the cardiovascular complications include chronic heart failure, cardiovascular death, stroke, myocardial infarction, coronary angioplasty associated restenosis, diabetic retinopathy, diabetic nephropathy and diabetic neuropathy, fewer coronary artery collateral blood vessels and myocardial ischemia. In other embodiments, the reducing oxidative stress is achieved by anti-oxidant therapy. In another embodiment, the anti-oxidant therapy is administration of a vitamin E or an analog, metabolite or derivative In another embodiment, a kit is provided comprising an anti-haptoglobin monoclonal antibody, binding fragment or recombinant protein as described herein, and instructions for use of said monoclonal antibody for determining the haptoglobin phenotype of a subject. In another embodiment, the anti-haptoglobin monoclonal antibody, binding fragment or recombinant protein comprises a detectable label or reporter; the label can be, by way of non-limiting example, an enzyme such as horseradish peroxidase or alkaline phosphatase. In another embodiment the label is a fluorophore. In a further embodiment, the kit includes instructions that indicate that the results of the test are useful for determining a potential of the subject to benefit from reducing oxidative stress or anti-oxidant therapy for vascular complications, wherein the presence of Hp 2-2 indicates a greater benefit of reducing oxidative stress or anti-oxidant therapy and thereby reducing the incidence of cardiovascular complications.

In another embodiment, methods are provided for identifying antibodies that differentially detect allelic variants of a polymorphic protein by following the steps of: 1) obtaining a plurality of monoclonal antibodies following the immunizing of an animal with the allelic variant of the polymorphic protein that is different than that allelic variant desirably differentially detected; 2) screening the plurality of monoclonal antibodies for differentially detecting a desired allelic variant, under conditions wherein differential reactivity is detectable, and 3) identifying monoclonal antibodies that differentially detect the desired allelic variant. In one embodiment the screening comprises binding a polyclonal anti-polymorphic protein antibody to a substrate in a plurality of separate locations, incubating the plurality of said locations with samples of the allelic variants of the polymorphic protein, subsequently incubating the plurality of locations with the monoclonal antibody, then detecting the binding of the monoclonal antibody at the plurality of locations. In one embodiment the polyclonal anti-polymorphic protein binds to all allelic variants. In one embodiment the monoclonal antibody is detectably labeled. In another embodiment the monoclonal antibody is not labeled and a detectably labeled binding partner to the monoclonal antibody is used to detect the bound monoclonal antibody. In another embodiment, the conditions comprise further dilution of the monoclonal antibody below the concentration wherein no differential detection of the allelic variants of the polymorphic protein occurs. In another embodiment the concentration is 10-1000-fold lower. In another embodiment, the differential detection is identified by variations in binding of the monoclonal antibody at greater dilutions, such as but not limited to 2,000-10,000. In another embodiment, the differential detection of certain allelic variants is identified by utilizing a sample at a higher concentration than that where no differential detection of the allelic variants of the polymorphic protein occurs. In another embodiment the allelic variants are human. In another embodiment, the polymorphic protein is haptoglobin. In another embodiment, the antibodies differentially detect with Hp 2-2 as compared to Hp 2-1, and differentially detect Hp 2-1 as compared with Hp 1-1. In another embodiment, Hp 2-2 is more desirably detected than Hp 2-1, and in another embodiment, Hp 2-1 is more desirably detected than Hp 1-1. In another embodiment the haptoglobin isoforms are human.

In another embodiment, an antibody identified as embodied herein is useful in an immunoassay when employed as both the capture antibody and the detection antibody. In another embodiment, the detection antibody is detectably labeled. In another embodiment, the binding of the detection antibody is quantitated using a detectably labeled binding partner to the detection antibody.

In another embodiment, the present invention provides a method of testing an antibody or recombinant protein for a utility in distinguishing between Hp 1-1, Hp 2-1, and Hp 2-2, comprising (a) immobilizing an anti-haptoglobin antibody on a substrate to form an antibody-substrate complex; (b) contacting a first quantity of the antibody-substrate complex with an Hp 1-1 molecule; (c) contacting a second quantity of the antibody-substrate complex with an Hp 2-1 molecule; (d) contacting a third quantity of the antibody-substrate complex with an Hp 2-2 molecule; (e) contacting the products of steps (b), (c), and (d) with the test antibody or recombinant protein; and (e) quantitatively determining a binding or interaction between the test antibody or recombinant protein and the Hp 1-1, Hp 2-1 and Hp 2-2; whereby a value obtained from the quantitatively determining that is characteristic of the presence of each of Hp 1-1, Hp 2-1 or Hp 2-2 indicates that the test antibody distinguishes between Hp 1-1, Hp 2-1 and Hp 2-2. In another embodiment the haptoglobin isoforms are human.

DETAILED DESCRIPTION OF THE PRESENT INVENTION

In one embodiment, the present invention provides anti-haptoglobin (Hp) monoclonal antibodies that bind with greater affinity to Hp 2-2 than to Hp 2-1, and with greater affinity to Hp 2-1 than to Hp 1-1. Hp 2-2 refers, in one embodiment, to polymers of haptoglobin comprising Hp 2 but no Hp 1. Hp 2-1 refers, in one embodiment, to polymers of haptoglobin comprising both Hp 1 and Hp 2. Hp 1-1 refers, in one embodiment, to polymers of haptoglobin comprising Hp 1 but no Hp 2. In certain embodiments, the haptoglobin isoforms are human.

In one embodiment, the antibody of the present invention is a monoclonal antibody. The term "monoclonal antibody" (mAb) refers, in one embodiment, to an antibody obtained from a population of substantially homogeneous antibodies, i.e., the individual antibodies comprising the population are identical except for possible naturally occurring mutations that may be present in minor amounts. Monoclonal antibodies may be highly specific, directed against a single antigenic site. In addition to their specificity, the monoclonal antibodies are advantageous in that they can be synthesized by host cells in a hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al, Nature 256: 495 (1975), or may be made by recombinant DNA methods (see, e.g., U.S. Pat. No. 4,816,567). The "monoclonal antibodies" also include clones of antigen-recognition and binding-site containing antibody fragments (Fv clones) isolated from phage antibody libraries using the techniques described in Clackson et al., Nature, 352:624-628 (1991) and Marks et al., J. Mol. Biol., 222:581-597 (1991), for example. Each type of antibody represents a separate embodiment of the present invention.

In another embodiment, the antibodies are monoclonal antibodies designated 1E10, 1G1, 2B3, 3H3, 4F9, 4G12, 4D3, 4D6 or the murine hybridoma deposited with the ATCC with a patent deposit designation PTA-9815.

Monoclonal antibodies can be raised in any animal species. In another embodiment, an anti-haptoglobin monoclonal antibody is that produced by the murine hybridoma deposited with the ATCC with a patent deposit designation PTA-9815. In another embodiment, a composition of the aforementioned antibody or an antigen-binding fragment thereof is provided.

The polymorphic protein can be a human protein, or it can be from an animal such as a domesticated or livestock animal, in which detection of particular isoforms of the polymeric protein are diagnostically, prognostically or therapeutically useful. Such domesticated animals include dogs, cats, hamsters, ferrets, rabbits and rodents including rats and mice. Livestock animals include, for example, cows, sheep, and buffalo. These are not meant to be limiting as, for example, zoo animals are also included. In the instance wherein the polymorphic protein is haptoglobin, the haptoglobin can be human.

In one embodiment, the terms "antibody" and "immunoglobulin" are used interchangeably herein. These terms are well understood by those in the field, and refer to a glycosylated (comprising sugar moieties) protein consisting of one or more polypeptides that specifically binds an antigen. One form of antibody constitutes the basic structural unit of an antibody. This form is a tetramer and consists of two identical pairs of antibody chains, each pair having one light and one heavy chain. In each pair, the light and heavy chain variable regions are together responsible for binding to an antigen, and the constant regions are responsible for the antibody effector functions.

Depending on the amino acid sequence of the constant domain of their heavy chains, intact antibodies can be assigned to different "classes". There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. Full-length immunoglobulin "light chains" (of about 25 kDa or about 214 amino acids) comprise a variable region of about 110 amino acids at the $NH_2$-terminus and a kappa or lambda constant region at the COOH-terminus Full-length immunoglobulin "heavy chains" (of about 50 kDa or about 446 amino acids), similarly comprise a variable region (of about 116 amino acids) and one of the aforementioned heavy chain constant regions or classes, e.g., gamma (of about 330 amino acids). The subunit structures and three-dimensional configurations of different classes of immunoglobulins are well known.

In another embodiment, the terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme that generates a detectable product, a fluorescent protein or other fluorescent moiety (fluorophore), and the like. The antibodies may be further conjugated to other moieties, such as members of specific binding pairs, e.g., biotin (member of biotin-avidin specific binding pair), a toxin, e.g. tetanus toxoid, and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. All of this is well know in the art.

In another embodiment, antibodies may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)) and in single chains (e.g., Huston et al., Proc. Natl. Acad. Sci. U.S.A., 85, 5879-5883 (1988) and Bird et al., Science, 242, 423-426 (1988), which are incorporated herein by reference). (See, generally, Hood et al., "Immunology", Benjamin, N.Y., 2nd ed. (1984), and Hunkapiller and Hood, Nature, 323, 15-16 (1986)).

In another embodiment, chimeric antibodies are antibodies whose light and heavy chain genes have been constructed, typically by genetic engineering, from antibody variable and constant region genes belonging to different species. For example, the variable segments of the genes from a mouse monoclonal antibody may be joined to human constant segments, such as gamma 1 and gamma 3. An example of a therapeutic chimeric antibody is a hybrid protein composed of the variable or antigen-binding domain from a rabbit antibody and the constant or effector domain from a human antibody (e.g., the anti-Tac chimeric antibody made by the cells of A.T.C.C. deposit Accession No. CRL 9688), although other mammalian species may be used.

In some embodiments, humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin.

In one embodiment, the term "framework region" or "FR" are those variable domain residues other than the hypervariable region residues. The framework regions have been precisely defined. See, e.g., Kabat, E. A. et al., Sequences of Proteins of Immunological Interest, US Dept. Health and Human Services, National Institutes of Health, USA (5th ed. 1991). Each variable domain typically has four FRs identified as FR1, FR2, FR3 and FR4. In some embodiments, "FR" also refers to an antibody variable region comprising amino acid residues abutting or proximal to, but outside of the CDR regions i.e. regions which directly interact with the antigen, acting as the recognition element of the antibody molecule within the variable region of an antibody. In one embodiment, the term "framework region" is intended to mean each domain of the framework that is separated by the CDRs. In some embodiments, the sequences of the framework regions of different light or heavy chains are relatively conserved within a species. The combined heavy and light chain framework regions of an antibody serve to position and align the CDRs for proper binding to the antigen.

In one embodiment, the term "CDR" or "complementarity determining region" refers to amino acid residues comprising non-contiguous antigen combining sites found within the variable region of both heavy and light chain polypeptides. In other embodiments, the "CDR" is further defined using the Enhanced Chothia numbering scheme and the "Contact CDR" definition described herein. In other embodiments, the term "CDR" will comprise regions as described by Kabat et al., J. Biol. Chem. 252, 6609-6616 (1977) and Kabat et al., *Sequences of protein of immunological interest*. (1991), and Chothia and Lesk, *J. Mol. Biol.* 196:901-917 (1987) and MacCallum et al., *J. Mol. Biol.* 262:732-745 (1996). The amino acids of the CDRs of the variable domains were initially defined by Kabat, based on sequence variability, to consist of amino acid residues 31-35B (CDRH1), 50-65 (CDRH2), and 95-102 (CDRH3) in the human heavy chain variable domain (VH) and amino acid residues 24-34 (CDRL1), 50-56 (CDRL2), and 89-97 (CDRL3) in the human light chain variable domain (VL), using Kabat's numbering system for amino acid residues of an antibody. See Kabat et al., sequences of proteins of immunological interest, US Dept. Health and Human Services, NIH, USA (5th ed. 1991). Chothia and Lesk, J. Mol. Biol. 196:901-917 (1987) presented another definition of the CDRs based on residues that included in the three-dimensional structural loops of the variable domain regions, which were found to be important in antigen binding activity. Chothia et al. defined the CDRs as consisting of amino acid residues 26-32 (CDRH1), 52-56 (CDRH2), and 95-102 (CDRH3) in the human heavy chain variable domain (VH), and amino acid residues 24-34 (CDRL1), 50-56 (CDRL2), and 89-97 (CDRL3) in the human light chain variable domain (VL). Combining the CDR definitions of Kabat and Chothia, the CDRs consist of amino acid residues 26-35B (CDRH1), 50-65 (CDRH2), and 95-102 (CDRH3) in human VH and amino acid residues 24-34 (CDRL1), 50-56 (CDRL2), and 89-97 (CDRL3) in human VL, based on Kabat's numbering system.

In other embodiments, one or more conservative amino acid substitutions in one or more of the six CDR regions in an antibody are provided.

In another embodiment, the term "humanized antibody" or "humanized immunoglobulin" refers to a non-human (e.g., mouse or rabbit) antibody containing one or more amino acids (in a framework region, a constant region or a CDR, for example) that have been substituted with a correspondingly positioned amino acid from a human antibody. In general, humanized antibodies produce a reduced immune response in a human host, as compared to a non-humanized version of the same antibody. In other embodiments, CDR grafting may be provided, wherein the six CDR loops comprising the antigen-binding site are grafted into corresponding human framework regions, a procedure well known in the art.

In other embodiments, it is understood that the recombinant proteins or antibodies designed and produced by the present methods may have additional conservative amino acid substitutions which have substantially no effect on antigen binding or other antibody functions. By conservative substitutions is intended combinations such as those from the following groups: gly, ala; val, ile, leu; asp, glu; asn, gln; ser, thr; lys, arg; and phe, tyr.

In another embodiment, the term "specific binding" refers to the ability of an antibody to preferentially bind to a particular analyte that is present in a homogeneous mixture of different analytes. In certain embodiments, a specific binding interaction will discriminate between desirable and undesirable analytes in a sample, in some embodiments more than about 10 to 100-fold or more (e.g., more than about 1000- or 10,000-fold).

In certain embodiments, the affinity between a capture agent and analyte when they are specifically bound in a capture agent/analyte complex is characterized by a $K_D$ (dissociation constant) of less than $10^{-6}$ M, less than $10^{-7}$ M, less than $10^{-8}$ M, less than $10^{-9}$ M, less than $10^{-9}$ M, less than $10^{-11}$ M, or less than about $10^{-12}$ M or less.

In another embodiment, the "variable region" of a heavy or light antibody chain is an N-terminal mature domain of the chains. All domains, CDRs and residue numbers are assigned on the basis of sequence alignments and structural knowledge. Identification and numbering of framework and CDR residues is as described in by Chothia and others (Chothia Structural determinants in the sequences of immunoglobulin variable domain. J Mol Biol 1998; 278:457-79).

In other embodiments, VH is the variable domain of an antibody heavy chain. VL is the variable domain of an antibody light chain, which could be of the kappa (K) or of the lambda isotype. K-1 antibodies have the kappa-1 isotype whereas K-2 antibodies have the kappa-2 isotype and VL is the variable lambda light chain.

In one embodiment, the terms "determining," "measuring," and "assessing," and "assaying" are used interchangeably and include both quantitative and qualitative determinations.

In another embodiment, the terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, beta galactosidase, luciferase, etc.; and the like. The term may also include monoclonal antibodies provided herein. Polypeptides may be of any size, and the term "peptide" refers to polypeptides that are 8-50 residues (e.g., 8-20 residues) in length.

In another embodiment, the term "isolated," when used in the context of an isolated antibody, refers to an antibody of interest that is at least 60% free, at least 75% free, at least 90% free, at least 95% free, at least 98% free, and even at least 99% free from other components with which the antibody is associated with prior to purification.

In another embodiment, the antibody molecule produced by the methods provided herein includes any molecule, so long as it comprises the Fc region of an antibody. Examples include an antibody, an antibody fragment, a fusion protein comprising an Fc region, and the like. An antibody is a protein that is produced in the living body by immune reaction as a result of exogenous antigen stimulation and has an activity to specifically bind to a corresponding antigen. Examples of the antibody include an antibody secreted by a hybridoma cell prepared from a spleen cell of an animal immunized with an antigen; an antibody prepared by a genetic recombination technique, namely an antibody obtained by introducing an antibody gene-inserted antibody expression vector into a host cell; and the like. Specific examples include an antibody produced by a hybridoma, a humanized antibody, a human antibody and the like.

The "variable region" of an antibody contains the antigen binding determinants of the molecule, and thus determines the specificity of an antibody for its target antigen. The variable region is so named because it is the most distinct in sequence from other antibodies within the same isotype. The majority of sequence variability occurs in the complementarity determining regions (CDRs). There are 6 CDRs total, three each per heavy and light chain, designated VH CDR1 (or CDRH1), VH CDR2 (or CDRH2), VH CDR3 (or CDRH3), VL CDR1 (or CDRL1), VL CDR2 (or CDRL2), and VL CDR3 (or CDRL3). The variable region outside of the CDRs is referred to as the framework (FR) region. Although not as diverse as the CDRs, sequence variability does occur in the FR region between different antibodies. Overall, this characteristic architecture of antibodies provides a stable scaffold (the FR region) upon which substantial antigen binding diversity (the CDRs) can be explored by the immune system to obtain specificity for a broad array of antigens.

The antibodies, or modified molecules provided herein may be nonhuman, chimeric, humanized, or fully human Chimeric antibodies comprise the variable region of a non-human antibody, for example VH and VL domains of mouse or rat origin, operably linked to the constant region of a human antibody. In another embodiment, a "humanized" antibody refers to an antibody comprising a human framework region (FR) and one or more complementarity determining regions (CDR's) from a non-human (usually mouse or rat) antibody. The non-human antibody providing the CDR's is called the "donor" and the human immunoglobulin providing the framework is called the "acceptor". In another embodiment the modified molecules provided herein can comprise a humanized variable region.

The monoclonal antibodies herein that differentially detect Hp 2-2 vs. Hp 2-1 and Hp 2-1 vs. 1-1 were identified by immunizing mice with affinity-purified Hp 1-1, followed by screening supernatants from initial cultures for differential binding to Hp 2-2. In certain experiments, the haptoglobin variants were presented to the monoclonal antibody after binding to a polyclonal anti-Hp antibody bound to a plastic surface (microtiter plate well). It was found that among a large number of monoclonal antibodies, no differential detection of haptoglobin variants was seen using a relatively more concentrated monoclonal antibody. However, upon further dilution of the monoclonal "detecting" antibody, differential detection of Hp 2-2 was seen in some supernatants. Such differentially reactive monoclonal antibodies, after purification and conjugation with a detectable label, could be used as both capture and detection antibodies to differentially identify Hp 2-2 in samples. In certain embodiments, dilution of purified monoclonal antibody as detection antibody to more than 1:2000, and in other embodiments, more than 1:5000 and more than 1:10000, provides differential detection of allelic variants of haptoglobin.

In other embodiments, a dilution of 10-10,000 below the titer where no differential detection of the different isoforms of Hp is used. In other embodiments, the dilution is 1,000-5, 000.

In another embodiment, the present invention provides an antigen-binding fragment of an anti-haptoglobin (Hp) antibody that binds with greater affinity to a first haptoglobin isoform than to a second haptoglobin isoform. In another embodiment, the present invention provides an antibody or recombinant protein comprising the antigen-binding fragment of an anti-Hp antibody of the invention. In another embodiment, the present invention provides an antibody or recombinant protein comprising the CDR of an anti-Hp antibody of the invention. In one embodiment, the antibody may be monoclonal. In another embodiment, the antibody may be polyclonal. In another embodiment, the antibody may be humanized or chimeric. In another embodiment, the antibody may be an scFv antibody.

The present invention encompasses antibody variants of antibodies described herein. Antibody variant refers, in one embodiment, to an antibody that has an amino acid sequence that differs from the amino acid sequence of a parent antibody. Preferably, the antibody variant comprises a heavy chain variable domain or a light chain variable domain having an amino acid sequence that is not found in nature. Such variants necessarily have less than 100% sequence identity or similarity with the parent antibody. In one embodiment, the antibody variant will have an amino acid sequence having about 75% amino acid sequence identity or similarity with the amino acid sequence of either the heavy or light chain variable domain of the parent antibody. In another embodiment, the antibody variant will have about 77% sequence identity or similarity with either the heavy or light chain variable domain of the parent antibody. In another embodiment, the antibody variant will have about 80% sequence identity or similarity with either the heavy or light chain variable domain of the parent antibody. In another embodiment, the antibody variant will have about 83% sequence identity or similarity with either the heavy or light chain variable domain of the parent antibody. In another embodiment, the antibody variant will have about 85% sequence identity or similarity with either the heavy or light chain variable domain of the parent antibody. In another embodiment, the antibody variant will have about 87% sequence identity or similarity with either the heavy or light chain variable domain of the parent antibody. In another embodiment, the antibody variant will have about 90% sequence identity or similarity with either the heavy or light chain variable domain of the parent antibody. In another embodiment, the antibody variant will have about 92% sequence identity or similarity with either the heavy or light chain variable domain of the parent antibody. In another embodiment, the antibody variant will have about 95% sequence identity or similarity with either the heavy or light chain variable domain of the parent antibody. In another embodiment, the antibody variant will have about 97% sequence identity or similarity with either the heavy or light chain variable domain of the parent antibody. Identity or similarity with respect to this sequence is defined herein as the percentage of amino acid residues in the candidate sequence that are identical (i.e., same residue) with the parent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity. The antibody variant is generally one that has a longer hypervariable region (by one or more amino acid residues; e.g. by about one to about 30 amino acid residues and preferably by about two to about ten amino acid residues) than the corresponding hypervariable region of a parent antibody.

An "amino acid alteration" refers to a change in the amino acid sequence of a predetermined amino acid sequence. Exemplary alterations include insertions, substitutions and deletions.

An "amino acid insertion" refers to the introduction of one or more amino acid residues into a predetermined amino acid sequence The amino acid insertion may comprise a "peptide insertion" in which case a peptide comprising two or more amino acid residues joined by peptide bond(s) is introduced into the predetermined amino acid sequence. Where the amino acid insertion involves insertion of a peptide, the inserted peptide may be generated by random mutagenesis such that it has an amino acid sequence which does not exist in nature.

The inserted residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (ile): leucine (Leu); lysine (Lys); methionine (Met); phenylalanine (Phe); proline (Pro); serine (Ser); threonine (Thr); tryptophan (Trp); tyrosine (Tyr); and valine (Val).

Insertion of one or more non-naturally occurring amino acid residues is also encompassed by the definition of an amino acid insertion herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301-336 (1991). To generate such non-naturally occurring amino acid residues, the procedures of Noren et al. Science 244:182 (1989) and Eliman et al., supra, can be used. Briefly, these procedures involve chemically activating a suppressor tRNA with a non-naturally occurring amino acid residue followed by in vitro transcription and translation of the RNA.

An amino acid insertion "in a hypervariable region" refers to the introduction of one or more amino acid residues within a hypervariable region amino acid sequence.

An amino acid insertion "adjacent a hypervariable region" refers to the introduction of one or more amino acid residues at the N-terminal and/or C-terminal end of a hypervariable region, such that at least one of the inserted amino acid residues forms a peptide bond with the N-terminal or C-terminal amino acid residue of the hypervariable region in question.

An "amino acid substitution" refers to the replacement of an existing amino acid residue in a predetermined amino acid sequence with another different amino acid residue. Each type of antibody variant described herein represents a separate embodiment of the present invention.

It is to be understood that any peptide of the present invention may, in one embodiment, be isolated, generated synthetically, obtained via translation of sequences subjected to any mutagenesis technique, as well as obtained via any protein evolution techniques, known to those skilled in the art.

In another embodiment, recombinant protein production is a means whereby peptides of the invention are produced. The recombinant proteins may then, in some embodiments, be introduced into an organism. Any method of generating proteins or peptides known in the art represents a separate embodiment of the present invention.

Antibody "binding affinity" may be determined by equilibrium methods (e.g. enzyme-linked immunoabsorbent assay (ELISA) or radioimmunoassay (RIA)), or kinetics. Methods for assessing antibody binding affinity are well known in the art, and are described, for example, in Ravindranath M et al, J Immunol Methods 169: 257-72, 1994;

Schots A et al, J Immunol Methods 109: 225, 1988; and Steward M et al, Immunology 72: 99-103, 1991; and Garcia-Ojeda P et al, Infect Immun 72: 3451-60, 2004. Each technique represents a separate embodiment of the present invention.

In another embodiment, the present invention provides an isolated nucleic acid encoding any anti-haptoglobin (Hp) antibody of the present invention. In another embodiment, the present invention provides an isolated nucleic acid encoding any antigen-binding fragment of the present invention.

In one embodiment of the present invention, "nucleic acid" refers to a string of at least two base-sugar-phosphate combinations. The term includes, in one embodiment, deoxyribonucleic acid (DNA) and ribonucleic acid (RNA). "Nucleotide" refers, in one embodiment, to a monomeric unit of a nucleic acid polymer. RNA may be in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) or ribozymes. The use of siRNA and miRNA has been described (Caudy A A et al, Genes & Devel 16:2491-96 (2002), Paddison P J et al., Methods Mol. Biol. 265:85-100 (2004), Paddison P J et al., Proc Natl Acad Sci USA. 99:1443-8 (2002) and references cited therein). DNA may be in the form of plasmid DNA, viral DNA, linear DNA, or chromosomal DNA or derivatives of these groups. In addition, these forms of DNA and RNA may be single, double, triple, or quadruple stranded. The term also includes, in one embodiment, artificial nucleic acids that may contain other types of backbones but the same bases. Examples of artificial nucleic acids are PNAs (peptide nucleic acids), phosphorothioates, and other variants of the phosphate backbone of native nucleic acids. PNA may contain peptide backbones and nucleotide bases, and may be able to bind both DNA and RNA molecules. The use of phosphothiorate nucleic acids and PNA are known to those skilled in the art, and are described in, for example, Nielsen P E, Curr Opin Struct Biol 9:353-57 (1999), Nielsen P E., Mol. Biotechnol. 26:233-48 (2004), Rebuffat A G et al., FASEB J. 16:1426-8 (2002), Inui T et al., J. Biol. Chem. 272:8109-12 (1997), Chasty R et al., Leuk Res. 20:391-5 (1996) and references cited therein; and Raz N K et al Biochem Biophys Res Commun. 297:1075-84. In another embodiment, the term includes any derivative of any type of RNA or DNA known in the art. The production and use of nucleic acids is known to those skilled in art and is described, for example, in Molecular Cloning, Sambrook and Russell, eds. (2001), and Methods in Enzymology: Guide to Molecular Cloning Techniques (2001) Berger and Kimmel, eds. Each nucleic acid derivative represents a separate embodiment of the present invention.

The nucleic acids can be produced by any synthetic or recombinant process that is known in the art. Nucleic acids can further be modified to alter biophysical or biological properties by means of techniques known in the art. For example, the nucleic acid can be modified to increase its stability against nucleases (e.g., "end-capping"), or to modify its lipophilicity, solubility, or binding affinity to complementary sequences.

DNA according to the invention can also be chemically synthesized by any method known in the art. For example, the DNA can be synthesized chemically from the four nucleotides in whole or in part by methods known in the art. Such methods include those described in Caruthers M H, Science 230:281-(1985). DNA can also be synthesized by preparing overlapping double-stranded oligonucleotides, filling in the gaps, and ligating the ends together (see, generally, Molecular Cloning (ibid) and Glover R P et al., Rapid Commun Mass Spectrom 9:897-901, 1995). DNA expressing functional homologues of the protein can be prepared from wild-type DNA by site-directed mutagenesis (see, for example, Molecular Biology Current Innovations and Future Trends. A. M. Griffin and H. G. Griffin, Eds. (1995); and Kim D F et al, Cold Spring Harb Symp Quant Biol. 66:119-26 (2001). The DNA obtained can be amplified by methods known in the art. One suitable method is the polymerase chain reaction (PCR) method described in Molecular Cloning (ibid). Each of these methods represents a separate embodiment of the present invention.

Methods for modifying nucleic acids to achieve specific purposes are disclosed in the art, for example, in Molecular Cloning (ibid). Moreover, the nucleic acid sequences of the invention can include one or more portions of nucleotide sequence that are non-coding for the protein of interest. Variations in the DNA sequences, which are caused by point mutations or by induced modifications (including insertion, deletion, and substitution) to enhance the activity, half-life or production of the polypeptides encoded thereby, are also encompassed in the invention. Each of these methods and variations represents a separate embodiment of the present invention.

In another embodiment, the present invention provides a vector comprising any nucleic acid of this invention. In another embodiment, the present invention provides a cell or packaging cell line comprising any antibody, peptide, or nucleic acid of this invention. In one embodiment, "vector" refers to a vehicle that facilitates expression of a nucleic acid molecule inserted therein in a cell. In another embodiment, a vector may facilitate expression in an expression system such as a reticulocyte extract. A vector may, in one embodiment, comprise a nucleic acid comprising non-coding nucleic acid sequences or coding sequences other than the inserted nucleic acid.

A large number of vectors known in the art may be used in this embodiment. A vector may include, in some embodiments, an appropriate selectable marker. In other embodiments, the vector may further include an origin of replication, or may be a shuttle vector, which can propagate both in bacteria, such as, for example, E. coli (wherein the vector comprises an appropriate selectable marker and origin of replication) or be compatible for propagation in vertebrate cells, or integration in the genome of an organism of choice. The vector according to this aspect of the present invention may be, for example, a plasmid, a bacmid, a phagemid, a cosmid, a phage, a modified or unmodified virus, an artificial chromosome, or any other vector known in the art. Many such vectors are commercially available, and their use is well known to those skilled in the art (see, for example, Molecular Cloning. (2001), Sambrook and Russell, eds.). Each vector represents a separate embodiment of the present invention.

In another embodiment, the nucleotide molecule present in the vector may be a plasmid, cosmid, or the like, or a vector or strand of nucleic acid. In another embodiment, the nucleotide molecule may be genetic material of a living organism, virus, phage, or material derived from a living organism, virus, or phage. The nucleotide molecule may be, in one embodiment, linear, circular, or concatemerized, and may be of any length. Each type of nucleotide molecule represents a separate embodiment of the present invention.

According to another embodiment, nucleic acid vectors comprising the isolated nucleic acid sequence include a promoter for regulating expression of the isolated nucleic acid. Such promoters are known to be cis-acting sequence elements required for transcription, as they serve to bind DNA-dependent RNA polymerase, which transcribes sequences present downstream thereof. Each vector disclosed herein represents a separate embodiment of the present invention.

In one embodiment, the isolated nucleic acid may be subcloned into the vector. "Subcloning", in all the applications disclosed herein, refers, in one embodiment, to inserting an oligonucleotide into a nucleotide molecule. For example, in one embodiment isolated DNA encoding an RNA transcript can be inserted into an appropriate expression vector that is suitable for the host cell such that the DNA is transcribed to produce the RNA.

The insertion into a vector can, in one embodiment, be accomplished by ligating the DNA fragment into a vector that has complementary cohesive termini. However, if the complementary restriction sites used to fragment the DNA are not present in the cloning vector, the ends of the DNA molecules may, in another embodiment, be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. Methods for subcloning are known to those skilled in the art, and are described, for example in Molecular Cloning (2001), Sambrook and Russell, eds. Each of these methods represents a separate embodiment of the present invention.

"Packaging cell line" refers, in one embodiment, to a cell comprising all or a portion of a viral genome and capable of producing viral particles. In one embodiment, the packaging cell line requires that additional viral sequences be supplied exogenously (for example, in a vector, plasmid, or the like) in order to produce viral particles. In another embodiment, the packaging cell line does not require additional viral sequences to produce viral particles. The construction and use of packaging cell lines is well known in the art, and is described, for example, in U.S. Pat. No. 6,589,763 and Kalpana G V et al, Semin Liver Disease 19:27-37 (1999). Each packaging cell line known in the art represents a separate embodiment of the present invention.

In another embodiment, the present invention provides a method of determining a haptoglobin type of a subject, comprising (a) contacting a biological sample of the subject with an anti-haptoglobin antibody; and (b) quantitatively determining a binding or interaction between the haptoglobin protein and the antibody under conditions whereby a value obtained from the quantitatively determination is characteristic of a presence of Hp 1-1, Hp 2-1, or Hp 2-2 in the biological sample. For example, Hp 1-1,2-1, and 2-2 produce characteristic values in a sandwich ELISA assay utilizing the 4G12 antibody of the present invention.

In another embodiment, the biological sample is serum. In a further embodiment the biological sample is plasma. In other embodiments, the plasma is plasma that has been anticoagulated with citrate, heparin or EDTA.

In one embodiment, the anti-haptoglobin (Hp) antibody utilized in the method may bind with greater affinity to Hp 2-2 than to Hp 2-1. In another embodiment, the anti-haptoglobin (Hp) antibody utilized in the method may not bind with greater affinity to Hp 2-2 than to Hp 2-1. In one embodiment, the anti-haptoglobin (Hp) antibody utilized in the method may bind with greater affinity to Hp 2-1 than to Hp 1-1. In another embodiment, the anti-haptoglobin (Hp) antibody utilized in the method may not bind with greater affinity to Hp 2-1 than to Hp 1-1. In another embodiment, the anti-haptoglobin (Hp) antibody utilized may be any antibody that binds to haptoglobin. In another embodiment, the antibodies are monoclonal antibodies designated 1E10, 1G1, 2B3, 3H3, 4F9, 4G12, 4D3, and 4D6. The hybridoma producing monoclonal antibody 4G12 has been deposited with the ATCC with a patent deposit designation PTA-9815.

In one embodiment, the method of the present invention may yield a value characteristic of the presence of Hp 1-1, Hp 2-1, or Hp 2-2 over a range of haptoglobin concentrations between about 0.15 grams per liter and about 2.5 grams per liter. In another embodiment, the method of the present invention distinguishes between Hp 1-1, 2-1, and 2-2 over the physiological range of haptoglobin concentration. In another embodiment, the method of the present invention distinguishes between Hp 1-1, 2-1, and 2-2 only over a narrower range of haptoglobin concentration. In one embodiment, the ability of the method of the present invention to distinguish between Hp 1-1, 2-1, and 2-2 is unaffected by hemolysis. In another embodiment, the ability of the method of the present invention to distinguish between Hp 1-1, 2-1, and 2-2 is unaffected by hemolysis. Each method represents a separate embodiment of the present invention.

In another embodiment, methods are provided for identifying antibodies that differentially detect allelic variants of a polymorphic protein by following the steps of: 1) obtaining a plurality of monoclonal antibodies by immunizing an animal with the allelic variant of the polymorphic protein that is different than that allelic variant desirably differentially detected; 2) screening the plurality of monoclonal antibodies for differentially detecting a desired allelic variant, under conditions wherein differential reactivity is detectable, and 3) identifying monoclonal antibodies that differentially detect the desired allelic variant. In one embodiment the screening comprises binding a polyclonal anti-polymorphic protein antibody to a substrate in a plurality of separate locations, incubating the plurality of said locations with samples of the allelic variants of the polymorphic protein, subsequently incubating the plurality of locations with the monoclonal antibody, then detecting the binding of the monoclonal antibody at the plurality of locations. In one embodiment the polyclonal anti-polymorphic protein binds to all allelic variants. In one embodiment the monoclonal antibody is detectably labeled. In another embodiment the monoclonal antibody is not labeled and a detectably labeled binding partner to the monoclonal antibody is used to detect the bound monoclonal antibody. In another embodiment, the conditions comprise further dilution of the monoclonal antibody as detection antibody below the concentration at which no differential detection of the allelic variants of the polymorphic protein occurs. In another embodiment the concentration is 10-fold lower. In other embodiments the concentration is 100-fold lower. In some embodiments the dilution of purified monoclonal antibody is 1:2000, and in other embodiments, 1:5000 and 1:10000, or even more dilute. As seen in the examples below, use of supernatants from monoclonal antibody cultures did not show differentiation of detectability of haptoglobin, but upon dilution to 1:2000 or greater, differences in binding to the allelic variations of haptoglobin was evident, the greatest differentiation at 1:4000 dilution. Thus, utility of monoclonal antibodies for differential detection is not evident from higher concentrations of antibody such as use of supernatants, and further dilution provides conditions in which differentiation occurs.

Thus, in another embodiment, the differential detection is identified by variations in binding of the monoclonal antibody at greater dilutions. In another embodiment, the polymorphic protein is haptoglobin. In another embodiment, the antibodies differentially detect with Hp 2-2 as compared to Hp 2-1, and differentially detect Hp 2-1 as compared with Hp 1-1. In another embodiment, Hp 2-2 is more desirably detected than Hp 2-1, and in another embodiment, Hp 2-1 is more desirably detected than Hp 1-1.

In another embodiment, the sample concentration, for example, dilution of patient serum, is used to provide differentiation between allelic variants. As will be noted in the examples, the hook effect of loss of signal on increasing concentration of analyte utilizing the reagents described herein was seen more prominently with Hp 2-1 than for Hp 2-2. Thus, employing a sample in an immunoassay in any of the embodiments described herein at a higher concentration provides a means to differentiate between Hp 2-2 and Hp 2-1. This, in another embodiment, the differential detection of certain allelic variants is identified by utilizing a sample at a higher concentration than that where no differential detection of the allelic variants of the polymorphic protein occurs.

In another embodiment, an antibody identified as embodied herein is useful in an immunoassay when employed as both the capture antibody and the detection antibody. In another embodiment, the detection antibody is detectably labeled, for example by direct conjugation of a chromophore, fluorophore, or enzyme that can be easily detected. In other embodiments, the label is a radionuclide, chemiluminescent label, or colloidal gold. In one embodiment the enzyme is horseradish peroxidase. In another embodiment the label is colloidal gold. This and other such detection methods are well known in the art. In another embodiment, the binding of the detection antibody is quantitated using a detectably labeled binding partner to the detection antibody. In this embodiment, the detection antibody is not labeled. In one embodiment, the detectably labeled binding partner to the mouse monoclonal antibody is horseradish peroxidase-labeled goat anti-rabbit IgG.

In other embodiments, suitable detectable labels include enzymes, fluorophores (e.g., fluorescein isothiocyanate (FITC), phycoerythrin (PE), Texas red (TR), rhodamine, free or chelated lanthanide series salts, especially $Eu^{3(+)}$, to name a few fluorophores), chromophores, radioisotopes, chelating agents, dyes, colloidal gold, latex particles, ligands (e.g., biotin), and chemiluminescent agents. In one embodiment, rapid point-of-care rapid immunoassay dipsticks utilize colloidal gold as the visibly detectable label. In the instance where a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$ are used, known currently available counting procedures may be utilized. In the embodiments where the label is an enzyme, detection may be accomplished by any of the presently utilized colorimetric, spectrophotometric, fluorospectrophotometric, amperometric or gasometric techniques known in the art.

Direct labels are one example of labels that can be used according to the present invention. A direct label has been defined as an entity, which in its natural state, is readily visible, either to the naked eye, or with the aid of an optical filter and/or applied stimulation, e.g. ultraviolet light to promote fluorescence. Among examples of colored labels, which can be used according to the present invention, include metallic sol particles, for example, gold sol particles such as those described by Leuvering (U.S. Pat. No. 4,313,734); dye sole particles such as described by Gribnau et al. (U.S. Pat. No. 4,373,932) and May et al. (WO 88/08534); dyed latex such as described by May, supra, Snyder (EP-A 0 280 559 and 0 281 327); or dyes encapsulated in liposomes as described by Campbell et al. (U.S. Pat. No. 4,703,017). Other direct labels include a radionuclide, a fluorescent moiety or a luminescent moiety. In addition to these direct labeling devices, indirect labels comprising enzymes can also be used according to the present invention. Various types of enzyme linked immunoassays are well known in the art, for example, alkaline phosphatase and horseradish peroxidase, lysozyme, glucose-6-phosphate dehydrogenase, lactate dehydrogenase, urease, these and others have been discussed in detail by Engvall in Enzyme Immunoassay ELISA and EMIT in Methods in Enzymology, 70:419-439 (1980) and in U.S. Pat. No. 4,857,453.

In one embodiment, the method of the present invention may comprise enzyme-linked immunosorbent assay (ELISA). Methods for ELISA are well known in the art, and are described, for example, in U.S. Pat. No. 5,654,407. In one embodiment of this method, the concentration of antigen is measured using two kinds of monoclonal antibodies which recognize different epitopes of the antigen. In the first stage of this embodiment, an antigen-containing sample is placed on a measurement plate on which antibodies (capture antibodies) have been adsorbed; the antigens in sample are bound to the capture antibodies. In the second stage, the substances in the sample other than the antigen are washed off with a washing agent. Then, in the third stage, a solution of the detection antibodies, in one embodiment detectably labeled with reporter molecules, such as an enzyme or radioisotope, are poured on the plate; the labeled antibodies bind to the antigens having been bound to the primary antibodies. In another embodiment, the detection antibodies are not detectably labeled but a detectably labeled binding partner to the detection antibodies are used to identify the binding of the detection antibody or in other embodiments amplify its presence. In one embodiment, the detection antibodies may have the same specificity as the capture antibodies. In another embodiment the capture and detection antibodies are the same. In another embodiment, the detection antibodies may have a different specificity from the capture antibodies. Each type of method represents a separate embodiment of the present invention.

In other embodiments, the immunoassay substrate can be glass beads, latex particles, glass rods, paper, microparticles and the like. The assay may be an ELISA, latex particle agglutination, microfluidic, chromatographic, or any other form of immunoassay capable of identifying the polymorphic protein allelic variant or variants using at least one immunologic reagent such as an antibody, an antigen-binding fragment thereof or an artificial construct comprising the complementarity determining region of an antibody.

In one embodiment the detectably labeled binding partner can be a labeled anti-antibody, such as an enzyme labeled goat anti-mouse IgG to detect the binding of unlabeled mouse monoclonal antibody. In other embodiments a further layer of reagents may be used to quantitative binding, such as a biotin labeled binding partner and a detectably labeled avidin. These variants in ELISA and immunoassay methods including signal amplification methods are well known in the art.

Excessive labeled antibodies are, in one embodiment, fully rinsed away with washing agent, then the amount of the reporter molecules left in the measurement plate is measured by means of an enzyme activity reader or a liquid scintillation counter; and the observed values are used for the estimation of the quantity of antigens in the sample.

In another embodiment, the method of the present invention may comprise a reporter molecule without the use of a capture antibody. Each method represents a separate embodiment of the present invention.

In another embodiment, a point-of-care rapid immunoassay device, such as a dipstick that can be conducted in a medical practitioner's office or even at home, is provided to rapidly and facilely determine the presence of an allelic variant of a polymorphic protein desirably identified, such as Hp 2-2, Hp 2-1 or both. In one embodiment the results are obtained in less than one hour and in another embodiment, in as little as around 10 minutes. In one embodiment, a lateral flow device is provided that can utilize a drop of whole blood and conduct an immunoassay using colloidal gold as the visibly detectable label. A reader device can be used in conjunction with a dipstick immunoassay, in a further embodiment. Devices such as those described in U.S. Pat. Nos. 6,171,870 and 6,673,628, are provided by way of non-limiting illustration.

In another embodiment, any method of the present invention may be utilized to test a subject for susceptibility to diabetic complications. In one embodiment, diabetic complications refers to vascular complications. In another embodiment, diabetic complications refers to restenosis after PTCA or coronary artery stent implantation. In another embodiment, diabetic complications refers to diabetic nephropathy. In another embodiment, diabetic complications refers to risk of cardiovascular disease. In another embodiment, diabetic complications refers to mortality in a defined period following acute myocardial infarction. In another embodiment, diabetic complications refers to diabetic cardiovascular disease. In another embodiment, diabetic complications refers to diabetic retinopathy. In another embodiment, diabetic complications refers to any other type of complication of diabetes in which haptoglobin type may play a role. Each diabetic complication represents a separate embodiment of the present invention. In certain embodiments the subject is diabetic. In other embodiments the subject is a type 1 diabetic or a type 2 diabetic. In other embodiments the subject is at risk for developing type 1 or type 2 diabetes. In other embodiments the subject is at risk for developing type 1 or type 2 diabetes.

In another embodiment, the Hp immunoassay described herein can be used in combination with other assays including immunoassays to test for risk factors for cardiovascular disease such as high-sensitivity C-reactive protein (hsCRP) or diabetes markers such as HbA1c, which in combination with haptoglobin phenotyping can provide increased predictive value.

In a further embodiment, a combination assay comprising Hp quantification and Hp phenotyping is provided.

In another embodiment, the present invention provides a method of testing an antibody or recombinant protein for a utility in distinguishing between Hp 1-1, Hp 2-1, and Hp 2-2, comprising (a) contacting a first quantity of the antibody or recombinant protein with an Hp 1-1 molecule; (b) contacting a second quantity of the antibody or recombinant protein with an Hp 2-2 molecule; (c) contacting a third quantity of the antibody with an Hp 2-2 molecule; and (d) quantitatively determining a binding or interaction between the antibody or recombinant protein and the Hp 1-1, Hp 2-1, and Hp 2-2, whereby a value obtained from the quantitatively determination that is characteristic of the presence of each of Hp 1-1, Hp 2-1, or Hp 2-2 indicates that the antibody distinguishes between Hp 1-1, Hp 2-1, and Hp 2-2. In one embodiment of this method, the antibody or recombinant protein may be tested for utility in distinguishing between Hp 1-1, Hp 2-1, and Hp 2-2 when used as the capture antibody in a sandwich ELISA. Any method described herein may be used to test an antibody or recombinant protein for a utility in distinguishing between Hp 1-1, Hp 2-1, and Hp 2-2, and each method represents a separate embodiment of the present invention.

In one embodiment, the antibody may be further tested for an ability to distinguish between Hp 1-1, Hp 2-1, and Hp 2-2 over a range of different haptoglobin concentrations. In another embodiment, the antibody may be tested for an ability to distinguish between Hp 1-1, Hp 2-1, and Hp 2-2 at only a single haptoglobin concentration. Each of these methods represents a separate embodiment of the present invention.

In another embodiment, the present invention provides a method of testing an antibody or recombinant protein for a utility in distinguishing between Hp 1-1, Hp 2-1, and Hp 2-2, comprising (a) immobilizing an anti-haptoglobin antibody on a substrate to form an antibody-substrate complex; (b) contacting a first quantity of the antibody-substrate complex with an Hp 1-1 molecule; (c) contacting a second quantity of the antibody-substrate complex with an Hp 2-1 molecule; (d) contacting a third quantity of the antibody-substrate complex with an Hp 2-2 molecule; (e) contacting the products of steps (b), (c) and (d) with the test antibody or recombinant protein; and (f) quantitatively determining a binding or interaction between the test antibody or recombinant protein and the Hp 1-1, Hp 2-1, and Hp 2-2; whereby a value obtained from the quantitatively determination that is characteristic of the presence of each of Hp 1-1, Hp 2-1, or Hp 2-2 indicates that the test antibody distinguishes between Hp 1-1, Hp 2-1, and Hp 2-2.

In one embodiment, the antibody may be further tested for an ability to distinguish between Hp 1-1, Hp 2-1, and Hp 2-2 over a range of different haptoglobin concentrations. In another embodiment, the antibody may be tested for an ability to distinguish between Hp 1-1, Hp 2-1, and Hp 2-2 at only a single haptoglobin concentration. Each of these methods represents a separate embodiment of the present invention.

In one embodiment, the plurality of test antibodies screened is generated in an animal lacking an Hp 2-2 allele. Use of mice, an animal lacking an Hp 2-2 allele may, in one embodiment, favor the generation of antibodies that preferentially bind Hp 2-2 over Hp 2-1.

In another embodiment, the present invention provides a kit that comprises any method of determining a haptoglobin type of a subject, method of testing a subject for susceptibility to diabetic complications, method of testing an antibody or recombinant protein for a utility in distinguishing between Hp 1-1, Hp 2-1, and Hp 2-2, or method of distinguishing between two allelic variants of a polymorphic protein in a biological sample described in the present invention. Kits are packages that facilitate a diagnostic or other procedure by providing materials or reagents needed thereof in a convenient format. Dipsticks and other assay formats for ease of use and minimal sample and reagent handling are also fully embodied herein. In one embodiment the subject is a diabetic. In another embodiment the subject is a type 1 or a type 2 diabetic. In other embodiments the subject is at risk for developing type 1 or type 2 diabetes. In another embodiment, the biological sample is serum. In a further embodiment the biological sample is plasma. In other embodiments, the plasma is plasma that has been anticoagulated with citrate, heparin or EDTA.

In one embodiment, the kit may further comprise an apparatus for performing enzyme-linked immunosorbent assay (ELISA). In another embodiment, the kit may not comprise an apparatus for performing enzyme-linked immunosorbent assay (ELISA). Each type of kit represents a separate embodiment of the present invention.

In another embodiment, the present invention provides a composition comprising an isolated nucleic acid, polypeptide, vector, cell, or packaging cell line of this invention. In one embodiment, the composition may comprise a liposome or other vehicle for introducing the isolated nucleic acid into a cell or for introducing the nucleic acid into a patient.

Thus, a method is provided of determining a haptoglobin phenotype type of a subject, comprising a. contacting a biological sample of said subject with an anti-haptoglobin antibody of any one of claims 1-22 or an antigen binding fragment thereof, forming a bound complex between the anti-haptoglobin antibody and haptoglobin in the biological sample;

b. quantitatively determining a binding affinity between said haptoglobin and said anti-haptoglobin antibody; and c. comparing said quantitatively determined binding affinity with a value obtained from a quantitatively determined binding affinity of said anti-haptoglobin antibody or antigen binding fragment thereof to an isolated Hp 1-1, Hp 2-1, or Hp 2-2 isoform, wherein the binding affinity determined is indicative of the Hp allele type, thereby determining the allele type of Hp in said subject. In another embodiment, the biological sample is serum. In a further embodiment the biological sample is plasma. In other embodiments, the plasma is plasma that has been anticoagulated with citrate, heparin or EDTA.

In one embodiment the subject is a diabetic. In another embodiment the subject is a type 1 or a type 2 diabetic. In other embodiments the subject is at risk for developing type 1 or type 2 diabetes.

In a further embodiment, the bound anti-haptoglobin antibody-antigen complex can be immobilized on a substrate. The immobilizing can comprise binding anti-haptoglobin antibody or antigen binding fragment thereof to the substrate. In certain embodiment, the anti-haptoglobin antibody is a polyclonal anti-haptoglobin antibody, and in others, a monoclonal anti-haptoglobin antibody such as but not limited to monoclonal antibody designated 1E10, 1G1, 2B3, 3H3, 4F9, 4G12, 4D3, or 4D6.

In further embodiments of the aforementioned method, additional steps include:

a. contacting said immobilized complex with an additional quantity of said anti-haptoglobin antibody or antigen binding fragment thereof; and b. determining a binding affinity between said antigen and said additional quantity of said anti-haptoglobin antibody or antigen binding fragment thereof.

The additional anti-haptoglobin antibody can be any of the antibodies described herein throughout, or an antigen-binding fragment thereof.

As noted above in certain embodiments, the antibody, recombinant protein or antigen-binding fragment thereof that binds to the Hp 2-2 is form is provided at a dilution below the concentration wherein differential binding affinity is not observed. In certain embodiments the dilution is 10-1000 times below. In other embodiments it is 10-10,000 times below. In certain other embodiments it is 1,000-5,000 times below.

In other embodiments, a method of testing a subject for susceptibility to a diabetic complication such as a vascular complication is provided, the method comprising the step of determining the subject's haptoglobin allele type according to any of the methods embodied herein, wherein the presence of Hp 2-2 indicates higher susceptibility to a diabetic complication. In certain embodiments the diabetic complication is a vascular disease, a nephropathy, a retinopathy, a cardiovascular disease or a combination thereof. In one embodiment the subject is a diabetic. In another embodiment the subject is a type 1 or a type 2 diabetic. In other embodiments the subject is at risk for developing type 1 or type 2 diabetes.

In another embodiment, a method of testing an antibody or a recombinant protein for a utility in distinguishing between haptoglobin allele types Hp 1-1, Hp 2-1, or Hp 2-2 is provided, the method comprising the steps of:

a. contacting the antibody, recombinant protein or an antigen binding fragment thereof with a known concentration of isolated Hp 1-1 molecule, Hp 2-1 molecule and Hp 2-2 molecule, forming a complex; and b. quantitatively determining a binding affinity between said antibody, recombinant protein or antigen binding fragment thereof and said Hp 1-1, Hp 2-1, and Hp 2-2; whereby a significantly different binding affinity to each of Hp 1-1, Hp 2-1, and Hp 2-2 indicates that said antibody or recombinant protein is capable of distinguishing between Hp 1-1, Hp 2-1, and Hp 2-2, The aforementioned method can further comprise immobilizing the complex of said Hp 1-1, Hp 2-1, or Hp 2-2 and said antibody, recombinant protein or antigen binding fragment thereof.

The aforementioned method can further comprise:

a. contacting said complex with an additional quantity of said antibody, recombinant protein or antigen binding fragment thereof subsequent to said immobilizing; and b. determining a binding affinity between said Hp 1-1, Hp 2-1, or Hp 2-2 and said additional quantity of said antibody or recombinant protein.

In the foregoing embodiments, the additional antibody can be any of the antibodies described herein, or an antigen-binding fragment thereof.

In the foregoing method, the antibody, recombinant protein or antigen-binding fragment thereof can be provided at a dilution below the concentration wherein different binding affinity is not observed. In one embodiment, the dilution is 10-10,000 times below. In another embodiment the dilution is 1,000-5,000 times below.

In another embodiment, a method is provided for testing a diabetic subject for a potential to benefit from reducing oxidative stress or anti-oxidant therapy and thereby reducing the incidence of cardiovascular disease, comprising the step of determining the subject's haptoglobin phenotype according to any of the foregoing methods, wherein the presence of Hp 2-2 indicates a greater benefit of reducing oxidative stress or anti-oxidant therapy and thereby reducing the incidence of cardiovascular complications. In another embodiment, the cardiovascular complications include chronic heart failure, cardiovascular death, stroke, myocardial infarction, coronary angioplasty associated restenosis, diabetic retinopathy, diabetic nephropathy and diabetic neuropathy, fewer coronary artery collateral blood vessels and myocardial ischemia. In other embodiments, the reducing oxidative stress is achieved by anti-oxidant therapy. In another embodiment, the anti-oxidant therapy is administration of a vitamin E or an analog, metabolite or derivative thereof.

In another embodiment, a method of testing an antibody or a recombinant protein for a utility in distinguishing between allelic variants of a polymorphic protein is provided, the method comprising the steps of:

a. contacting the antibody, recombinant protein or an antigen binding fragment thereof with a known concentration of isolated allelic variants of a polymorphic protein; and b. quantitatively determining a binding affinity between said antibody, recombinant protein or antigen binding fragment thereof and said allelic variants; whereby a significantly different binding affinity to each of allelic variants indicates that said antibody or recombinant protein is capable of distinguishing there between.

In a further embodiment of the foregoing method, the complex of said allelic variants and said antibody, recombinant protein or antigen binding fragment thereof can be immobilized on a substrate.

In another embodiment the method can further comprise a. contacting said complex with an additional quantity of said antibody, recombinant protein or antigen binding fragment thereof subsequent to said immobilizing; and b. determining a binding affinity between said allelic variants and said additional quantity of said antibody or recombinant protein.

In the foregoing embodiments, the antibody, recombinant protein or antigen-binding fragment thereof is provided at a dilution below the concentration wherein different binding affinity is not observed. In one embodiment, the dilution is 10-10,000 times below. In another embodiment the dilution is 1,000-5,000 times below.

In another embodiment, a kit is provided comprising any one of the monoclonal antibodies described herein, and instructions for use of said monoclonal antibody for determining the haptoglobin phenotype of a subject. In other embodiments, the kit can include instructions for that indicate that the results of the test are useful for determining a potential of the subject to benefit from reducing oxidative stress or anti-oxidant therapy for vascular complications, wherein the presence of Hp 2-2 indicates a greater benefit of reducing oxidative stress or anti-oxidant therapy and thereby reducing the incidence of cardiovascular complications.

EXAMPLES

Example 1

Preparation and Screening of Monoclonal Antibodies

Immunization and hybridoma preparation. Monoclonal antibodies were raised using Balb c mice according to standard procedures. Immunizations were performed using affinity purified human Haptoglobin (Hp) 1-1. Mouse tail bleeds were screened for antibody titer to Hp using a standard ELISA assay. Specifically, 200 ng/well of Hp 1-1, Hp 2-1 and Hp 2-2 were coated onto plastic microtiter plates overnight at 4 C using a bicarbonate buffer. Plates were then blocked with 5% milk in PBS for 1 hour at room temp. Mouse tail bleeds were serially diluted and incubated onto the plates. Plates were washed and mouse antibody to the respective Hp phenotypes were detected using HRP labeled goat-anti-mouse IgG (H+L) at a dilution of 1:2000. Plates were washed again and HRP substrate (tetramethyl benzidine, TMB) and hydrogen peroxide was added for 10-30 minutes. Plates were read on a microtiter plate reader at 620 nm Positive signal was based on any absorbance over 3 times the background (buffer blank).

Fusion was initiated in mice whose tail bleed titers were greater than 1:30,000. Fusions were carried out according to standard protocols. Clones were plated out and supernatants at a dilution of 1:2 were used to detect antibody-producing cells. The screening assay for antibody clones was the same as the tail-bleed assay except that an additional plate was screened using HRP labeled goat-anti-mouse IgM. 480 clones were screened against purified Hp 1-1. The strongest 140 clones were expanded and rescreened against Hp 1-1, Hp 2-1 and Hp 2-2 coated plates using both anti-mouse IgG and IgM to detect antibody-producing clones. 21 clones were selected for further screening based on (1) reactivity (absorbance 620 nm>1.5000) against all 3 antigens and (2) no IgM response.

Assay to determine which antibody producing clones provided antibodies suitable for use in a sandwich enzyme immunoassay: The assay is designed to screen for antibodies that can bind human haptoglobin that is presented to the antibody in the same way as it is presented in a classic sandwich immunoassay. That is, an antibody bound to a solid support, binds native antigen (Haptoglobin) from patient samples which, in turn, is bound by antibody labeled with enzyme. The rabbit anti-human haptoglobin binds Hp from patient sera of known phenotype and the anti-human Hp monoclonal antibodies in the clone supernatant binds to the Hp bound to the rabbit antibody and it is, in turn, detected by goat-anti-mouse antibody labeled with enzyme. This allows screening of many supernatants for antibody without having to label the individual supernatant antibodies with enzyme. In the previously described ELISA assays, the human Hp is immobilized on a microtiter plate and may be denatured in the process. Therefore monoclonal antibodies that detect Hp immobilized on a plate may not be suitable for detecting Hp bound by a capture antibody in a sandwich EIA.

Microtiter plates were coated with 1ug/well of DEAE-purified rabbit-anti-human haptoglobin (Sigma) using a phosphate coating buffer, pH=6.5. Human sera from Hp 1-1, Hp 2-1 or Hp 2-2 were diluted 1:500 in sample diluting buffer (PBS with 1% BSA, 0.1% Tween 20 and a preservative) and 100 ul of diluted sample is added to plates coated with rabbit-anti-Hp. Samples were incubated for 1 hour at room temp (18 C-25 C) with shaking (750 rpm). Plates are then emptied and washed 5 times with Wash Buffer (PBS and 0.1% Tween 20). Care is taken to remove remaining buffer droplets. Clone supernatants are diluted in sample diluting buffer and 100 ul of each dilution is added to each well. Supernatants are incubated for 1 hour at room temp (18 C-25 C) with shaking (750 rpm). Plates are emptied and washed as before. 100 ul of HRP labeled goat-anti-mouse IgG (Pierce, diluted 1:15,000 or 1:20,000 in sample diluting buffer with DEAE purified Rabbit IgG, Biocheck, Inc. added) is added to each well. Conjugate is incubated at room temp (18 C-25 C) for 30 minutes with shaking (750 rpm) and emptied and washed as before. 100 ul of TMB solution (Biocheck, Inc.) and hydrogen peroxide is added to each well and incubated at room temperature for 20 minutes with shaking (750 rpm). 100 ul of 1N HCl is added to each well and the absorbance of each well is read at 450 nm in a Vmax Kinetic Microplate Reader. DEAE-purified, commercially available monoclonal anti-human haptoglobin (Sigma) was used as a positive control.

Twenty-one supernatants from clones which displayed anti-haptoglobin activity in the ELISA were titrated in the above assay to determine which supernatants produced antibodies that 1) react with all 3 phenotypes of Hp, and 2) are give the strongest signal at highest dilutions. At low dilutions all but 2 clones gave strong signals with all phenotypes except for clones 2F6 and 4D7, which did not react. This illustrates, that although they can detect Hp on a plate ELISA they were not suitable to for a sandwich enzyme immunoassay. High buffer only blanks indicated non-specific binding due to large amounts of mouse IgG being present. Further dilution of the supernatants eliminated this artifact.

Twenty-One Supernatants Diluted 1:2:

|  |  |  | Samples: | | | | | |
|---|---|---|---|---|---|---|---|---|
|  | 2nd MoAb: | Buffer only | 1-1 #10 | 1-1 #11 | 2-1 #2 | 2-1 #4 | 2-2 #1 | 2-2 #3 |
| Plate #1: | 1A12 | 1.566 | 4.000 | 4.000 | 4.000 | 4.000 | 4.000 | 4.000 |
|  | 1D1 | 1.568 | 4.000 | 4.000 | 4.000 | 4.000 | 4.000 | 4.000 |
|  | 1E9 | 0.832 | 4.000 | 4.000 | 4.000 | 4.000 | 4.000 | 4.000 |
|  | 1E10 | 0.280 | 4.000 | 4.000 | 4.000 | 4.000 | 4.000 | 4.000 |
|  | 1G1 | 0.485 | 4.000 | 3.992 | 4.000 | 4.000 | 4.000 | 4.000 |

|  | | Samples: | | | | | |
|---|---|---|---|---|---|---|---|
| 2nd MoAb: | Buffer only | 1-1 #10 | 1-1 #11 | 2-1 #2 | 2-1 #4 | 2-2 #1 | 2-2 #3 |
| | 2A9 | 0.450 | 4.000 | 4.000 | 4.000 | 4.000 | 4.000 | 4.000 |
| | 2B3 | 0.563 | 4.000 | 4.000 | 4.000 | 4.000 | 4.000 | 4.000 |
| | 2E4 | 0.245 | 4.000 | 4.000 | 4.000 | 4.000 | 4.000 | 4.000 |
| | 2F6 | 0.369 | 0.269 | 0.554 | 0.277 | 0.251 | 0.255 | 0.316 |
| | 3A1 | 0.443 | 4.000 | 4.000 | 4.000 | 4.000 | 4.000 | 4.000 |
| | 3B5 | 1.558 | 4.000 | 4.000 | 4.000 | 4.000 | 4.000 | 4.000 |
| | 0.01 ug/ml Sigma MoAb | 0.174 | 3.663 | 3.825 | 3.840 | 3.754 | 3.738 | 3.769 |
| Plate #2: | 3E6 | 0.558 | 3.935 | 4.000 | 3.960 | 3.947 | 3.983 | 3.969 |
| | 3E12 | 0.215 | 3.997 | 3.959 | 4.000 | 3.986 | 4.000 | 4.000 |
| | 3H3 | 2.254 | 3.944 | 3.963 | 3.972 | 3.964 | 4.000 | 3.983 |
| | 4D12 | 0.279 | 4.000 | 4.000 | 3.949 | 4.000 | 4.000 | 4.000 |
| | 4F9 | 0.178 | 3.938 | 3.917 | 3.973 | 3.894 | 4.000 | 4.000 |
| | 4G12 | 0.307 | 3.984 | 3.926 | 3.969 | 4.000 | 4.000 | 4.000 |
| | 4D3 | 0.489 | 3.992 | 3.974 | 3.980 | 3.945 | 3.962 | 4.000 |
| | 4D6 | 0.314 | 4.000 | 3.968 | 3.905 | 4.000 | 4.000 | 3.952 |
| | 4D7 | 0.245 | 0.174 | 0.199 | 0.171 | 0.184 | 0.209 | 0.205 |
| | 5D3 | 0.673 | 3.919 | 4.000 | 4.000 | 3.940 | 4.000 | 4.000 |
| | 0.01 ug/ml Sigma MoAb | 0.178 | 3.650 | 3.732 | 3.746 | 3.713 | 3.817 | 3.822 |

For the Negative Control, 1:1000 2-2 sample #3 was used with no addition of secondary antibody; substituted with buffer; and 1:15,000 Pierce GAM-HRP with 100 ug/ml rabbit IgG. For plate #1, the avg. OD was 0.127 (1.2% CV), and for plate #2, 0.126 (3.0% CV).

Experiments with more dilute supernatant. In this experiment, Hp 1-1 and Hp 2-2 were detected, using a supernatant dilution of 1:2000. Once the supernatant titration is further diluted, two classes of antibody were discovered: Class I, antibodies that detect Hp 1-1 and Hp 2-2 at equal intensity, and Class II, antibodies that have a much lower activity for Hp 1-1 than Hp 2-2. Eleven clones generated Class I antibodies and 8 clones generated Class II antibodies. The Sigma commercial anti-human antibody behaves as a Class I antibody. This data suggests that the Class II antibodies detect Hp phenotypes differently than the Class I monoclonals. Class II antibodies having the properties described herein are fully embodied herein.

| 2nd MoAb: | Buffer only | 1-1 #10 | 2-2 #1 |
|---|---|---|---|
| | | 1:2000 dilution of supernatant/1:20k | |
| | | GAM-HRP | |
| 1A12 Class I | 0.177 | 3.321 | 3.811 |
| 1D1 Class I | 0.160 | 3.132 | 3.332 |

| 2nd MoAb: | Buffer only | 1-1 #10 | 2-2 #1 |
|---|---|---|---|
| | | 1:2000 dilution of supernatant/1:20k | |
| 1E9 Class I | 0.147 | 3.899 | 4.000 |
| 1E10 Class II | 0.145 | 1.755 | 2.243 |
| 1G1 Class II | 0.143 | 1.964 | 2.403 |
| 2A9 Class I | 0.160 | 3.839 | 3.934 |
| 2B3 Class II | 0.143 | 1.603 | 2.270 |
| 2E4 Class I | 0.151 | 3.692 | 3.759 |
| 2F6 N/A | 0.133 | 0.181 | 0.237 |
| 3A1 Class I | 0.144 | 2.144 | 2.228 |
| 3B5 Class I | 0.154 | 3.172 | 3.024 |
| 3E6 Class I | 0.140 | 2.281 | 2.235 |
| 3E12 Class I | 0.148 | 3.123 | 3.569 |
| 3H3 Class II | 0.156 | 1.573 | 2.236 |
| 4D12 Class I | 0.160 | 3.826 | 3.960 |
| 4F9 Class II | 0.140 | 0.645 | 2.290 |
| 4G12 Class II | 0.133 | 0.722 | 2.704 |
| 4D3 Class II | 0.135 | 1.761 | 2.281 |
| 4D6 Class II | 0.128 | 2.847 | 3.402 |
| 4D7 N/A | 0.131 | 0.179 | 0.241 |
| 5D3 Class I | 0.139 | 2.858 | 2.742 |
| 0.01 ug/ml Sigma MoAb | 0.169 | 3.840 | 3.854 |

The 4 strongest Class I monoclonals and 1 Class II monoclonal (4G12) were selected and they were titrated to further dilutions versus all 3 Hp phenotypes. At 1:4000 dilution of the clone supernatants, the 4 Class I monoclonals continued to detect all 3 phenotype at the same level (C.V.<5%) while the Class II monoclonal detected the Hp phenotypes differently with Hp 1-1 signal<Hp 2-1 signal<Hp 2-2 signal. This data indicate that Class II monoclonals could differentiate between the 3 phenotypes of Hp. Use of dilute conditions of the monoclonal antibody in an assay that differentially detects Hp isoforms or phenotypes is one embodiment herein.

Condition: Coating Ab:Rabbit anti-Human Haptoglobin 1 ug/well; Secondary Ab: monoclonal antibody supernatants or Pan Reactive MoAb from Sigma; HRP conjugate: 1:20,000 Pierce goat anti-mouse IgG-HRP with 100 ug/ml rabbit IgG

| | | Samples: | | | | | | |
|---|---|---|---|---|---|---|---|---|
| 2nd MoAb: | Buffer only | 1-1 #10 | 2-1 #2 | 2-2 #1 | Buffer only | 1-1 #10 | 2-1 #2 | 2-2 #1 |
| | 1:5000 dilution of supernatant | | | | 1:4000 dilution of supernatant | | | |
| Plate #2: 1E9 | 0.122 | 2.506 | 2.605 | 2.458 | 0.120 | 2.995 | 3.103 | 2.970 |
| 2E4 | 0.120 | 2.464 | 2.360 | 2.486 | 0.119 | 2.900 | 2.887 | 2.936 |
| 3E6 | 0.128 | 1.384 | 1.249 | 1.245 | 0.115 | 1.684 | 1.572 | 1.543 |
| 4G12 | 0.117 | 0.415 | 1.128 | 1.452 | 0.117 | 0.495 | 1.382 | 1.819 |
| 5D3 | 0.122 | 1.417 | 1.265 | 1.302 | 0.145 | 1.764 | 1.592 | 1.596 |
| 0.01 ug/ml Sigma MoAb | 0.112 | 3.975 | 3.983 | 4.000 | 0.140 | 3.959 | 3.955 | 4.000 |

Negative Control: no addition of secondary antibody; substituted with buffer. 1:20,000 Pierce GAM-HRP with 100 ug/ml rabbit IgG:

| | Buffer only | 1-1 #10 | 2-1 #2 | 2-2 #1 |
|---|---|---|---|---|
| 1:5,000 | 0.120 | 0.086 | 0.095 | 0.088 |
| 1:4,000 | 0.116 | 0.083 | 0.096 | 0.089 |

Further studies on Class II clones; use as capture antibodies. Several Class II clones were scaled up in cell culture.

Monoclonal antibodies from the supernatants were purified using protein G columns. Purified monoclonal antibodies were coated separately on microtiter plates and also coupled to horseradish peroxidase (HRP). Different combinations of monoclonal capture and conjugate antibodies were tried to determine the optimum pair for a sandwich assay to identify the Hp phenotypes in human serum. The best monoclonal conjugate/capture antibody was 4G12.

Purified monoclonal 4G12 was coupled to microtiter plates at 1 ug/mL in 0.2M NaHCO3 buffer pH=6.5. Plates were coated overnight and dried. Dried plates were stored in plastic bags with desiccant. The 4G12 conjugate was prepared by treating 1 mg of purified 4G12 monoclonal with sodium periodate, followed by treatment with sodium borohydride. The conjugate is dialyzed and purified on an S-300 column, concentrated to 0.5 mg/ml in conjugate buffer (Biocheck, Inc). The conjugate is stored at 2-8 C. The conjugate was titered to determine the optimum concentration.

Twelve human sera of know Hp phenotype were diluted 1:1000 in diluting buffer. 100 ul of diluted serum was added to a microtiter plate coated with 4G12 monoclonal antibody. The plates are incubated with shaking at room temp, for 1 hour. The plates were emptied and washed 5 times with wash buffer. The plate was emptied and 100 ul of different dilutions of HRP-labeled 4G12 conjugate are added to the wells. The plate is incubated for 1 hour at room temp with shaking and washed 5 times with wash buffer. 100 ul of TMB substrate and hydrogen peroxide is added to each well, incubated at room temp for 30 minutes with shaking. 100 ul of 1N HCl is added to each well and the plate is read in a microplate reader at 450 nm within 15 minutes.

| Sample # | HRP conjugate: 1:5,000 4G12 Ab-HRP | 1:10,000 4G12 Ab-HRP |
|---|---|---|
| Buffer Only | 0.064 | 0.052 |
| 1-1 #10 | 0.107 | 0.080 |
| 1-1 #11 | 0.112 | 0.082 |
| 1-1 #44 | 0.131 | 0.149 |
| 2-1 #2 | 1.493 | 0.804 |
| 2-1 #4 | 2.658 | 1.304 |
| 2-1 #24 | 2.117 | 1.084 |
| 2-1 #36 | 1.987 | 0.965 |
| 2-2 #1 | 3.955 | 2.361 |
| 2-2 #3 | 3.457 | 1.813 |
| 2-2 #5 | 4.000 | 2.702 |
| 2-2 #6 | 4.000 | 2.945 |
| 2-2 #15 | 4.000 | 3.401 |

Data from this experiment shows that at both concentrations of 4G12 conjugate, the Hp 1-1, Hp 2-1 and Hp 2-2 samples can be differentiated. Specifically, at 1:5000 concentration, the Hp 1-1 samples all had absorbance below 0.131, the Hp 2-1 samples ranged between 1.493-2.658 and the Hp 2-2 samples were all over 3.457. All 12 samples' phenotypes were correctly identified.

In a further experiment, the effect of sample dilution on selectivity for Hp phenotype was investigated. The results are shown on the following table.

| Hp phenoype | Sample ID# | Undiluted Sample A450 | 1:10 diluted sample A450 | 1:25 diluted sample A450 | 1:50 diluted sample A450 | 1:100 diluted sample A450 | 1:1,000 diluted sample A450 |
|---|---|---|---|---|---|---|---|
| | Buffer Only | 0.045 | N/A | N/A | N/A | N/A | N/A |
| Hp 1-1 | Control 1-1 | 0.154 | 0.082 | 0.073 | 0.066 | 0.064 | 0.055 |
| Hp 2-1 | Control 2-1 | 1.121 | 1.604 | 1.629 | 1.567 | 1.505 | 1.005 |
| Hp 2-2 | Control 2-2 | 3.087 | 3.093 | 2.986 | 2.859 | 2.690 | 2.057 |
| Hp 2-2 | 9 | N/A | 2.133 | 1.989 | 1.790 | 1.679 | 0.871 |
| Hp 2-2 | 12 | N/A | 2.433 | 2.284 | 2.136 | 1.968 | 1.144 |
| Hp 2-2 | 13 | N/A | 2.562 | 2.353 | 2.196 | 2.052 | 1.344 |
| Hp 2-2 | 19 | N/A | 2.462 | 2.281 | 2.092 | 1.940 | 1.169 |
| Hp 2-2 | 23 | N/A | 2.654 | 2.454 | 2.327 | 2.162 | 1.255 |
| Hp 2-2 | 24 | N/A | 2.663 | 2.462 | 2.321 | 2.136 | 1.160 |
| Hp 2-2 | 25 | N/A | 2.540 | 2.322 | 2.221 | 2.044 | 1.168 |
| Hp 2-2 | 31 | N/A | 2.451 | 2.341 | 2.210 | 2.072 | 1.327 |
| Hp 2-2 | 34 | N/A | 2.338 | 2.235 | 2.110 | 1.979 | 1.187 |
| Hp 2-2 | 45 | N/A | 1.576 | 1.590 | 1.567 | 1.503 | 1.184 |
| Hp 2-2 | 118 | N/A | 1.614 | 1.618 | 1.599 | 1.563 | 1.327 |
| Hp 2-2 | 147 | N/A | 1.476 | 1.490 | 1.458 | 1.436 | 1.061 |
| Hp 2-2 | 148 | N/A | 1.746 | 1.750 | 1.715 | 1.682 | 1.335 |
| Hp 2-2 | 264 | N/A | 1.553 | 1.574 | 1.553 | 1.532 | 1.229 |
| Hp 2-2 | 268 | N/A | 1.555 | 1.536 | 1.501 | 1.427 | 1.024 |
| Hp 2-2 | BRH 196266 | 2.430 | 2.193 | 2.101 | 1.957 | 1.795 | 1.063 |
| Hp 2-2 | BRH 196284 | 2.361 | 2.175 | 2.029 | 1.874 | 1.665 | 0.326 |
| Hp 2-2 | BRH 196291 | 1.791 | 1.808 | 1.760 | 1.632 | 1.499 | 0.715 |
| Hp 2-2 | BRH 196293 | 2.292 | 2.124 | 2.002 | 1.864 | 1.696 | 0.913 |
| Hp 2-1 | BRH 196268 | 1.412 | 1.750 | 1.801 | 1.764 | 1.722 | 1.353 |
| Hp 2-1 | BRH 196292 | 1.233 | 1.612 | 1.664 | 1.606 | 1.604 | 1.249 |
| Hp 2-1 | BRH 196307 | 1.416 | 1.730 | 1.784 | 1.762 | 1.690 | 1.290 |
| Hp 2-1 | BRH 196314 | 1.320 | 1.739 | 1.796 | 1.779 | 1.697 | 1.305 |

A summary of these data are shown on the following table.

| | Looking at highest Hp 2-1 lowest Hp 2-2 vs | | | | | | |
|---|---|---|---|---|---|---|---|
| BRH 196291 | 1.791 | 1.808 | 1.760 | 1.632 | 1.499 | 0.715 | Hp 2-2 |
| BRH 196268 | 1.412 | 1.750 | 1.801 | 1.764 | 1.722 | 1.353 | Hp 2-1 |
| OD Hp 2-2/Hp 2-1 | 1.26841 3598 | 1.03314 2857 | 0.97723 487 | 0.92517 0068 | 0.87049 9419 | 0.52845 5285 | |
| Resolution (%) | 27% | 3.30% | −2% | −7% | −13% | −47% | |

Variables such as sample concentration, conjugate diluents, incubation times and sample stability were all examined. The assay demonstrates excellent reproducibility, linearity and accuracy. The assay requires under 2 hours to perform and has a sensitivity, specificity and accuracy for all 3 phenotypes of greater than 95%.

Thus, as a result of immunization of mice with Hp 1-1 antigen, two different classes of anti-haptoglobin monoclonals were identified, one class with the ability to differentiate between the three variants of Hp in human plasma. The ability of the monoclonals to differentiate was enhanced by selecting the optimum concentration of HRP-class II monoclonal conjugate used in the assay. Use of such an optimized concentration is embodied herein.

Example 2

Antibody Sequence

The nucleotide and amino acid sequences of the heavy and light chains of antibody 4G12 were determined by standard methods as described below.

mRNA preparation. mRNA was extracted from $3 \times 10^6$ 4G12 hybridoma cells. The light chain variable region pseudo gene mRNA produced by the myeloma cells was digested. 5' RACE was performed in which an adaptor was ligated to the 5' end of the variable region mRNA.

RT-PCR. Reverse transcription was performed to create cDNA, which was amplified using outer and inner PCR reactions. Each PCR reaction used one adaptor-specific primer and one immunoglobulin constant region-specific primer. The heavy chain outer PCR product (approximate size of 500 bp) was extracted from the gel and purified. An inner PCR was performed on the light chain to create additional PCR product. The light chain inner PCR product (approximate size of 500 bp) was extracted from the gel and purified.

Cloning. Purified PCR products resulting from the heavy and light chain variable region immunoglobulin were ligated into Invitrogen's TOPO TA cloning vectors and transformed into TOP10 cells. The clones were screened by PCR to find those with the correct-sized insert. Three clones for the light chain and three clones for the heavy chain, which contained the correct-sized insert were scaled-up, purified and cycle sequenced.

The light chain nucleotide sequence is depicted in SEQ ID NO:1, and the amino acid sequence in SEQ ID NO:2. The light chain complementarity determining regions 1, 2 and 3 are SEQ ID NO:3, SEQ ID NO:4 and SEQ ID NO:5, respectively.

The heavy chain nucleotide sequence is depicted in SEQ ID NO:6, and the amino acid sequence SEQ ID NO:7. The heavy chain complementarity determining regions 1, 2 and 3 are SEQ ID NO:8, SEQ ID NO:9 and SEQ ID NO:10, respectively.

Example 3

Enzyme Immunoassay for the Qualitative Determination of Haptoglobin 2-2 in Diabetic Serum and Plasma The following describes a typical immunoassay kit utilizing a Hp monoclonal antibody embodied herein that differentially detects Hp 2-2. The description of the kit, its components and other features are merely exemplary and non-limiting as to the embodiments encompassed herein. The immunoassay may be practiced in any of a number of other formats without deviating from the teachings herein.

Intended use. The kit is an enzyme immunoassay for the qualitative determination of Haptoglobin 2-2 in human serum and plasma to be used in conjunction with clinical evaluation and patient risk assessment as an aid in predicting risk of myocardial infarction and death from cardiovascular disease in individuals with diabetes. The kit is for use in a professional laboratory only.

Test principle. The kit is a qualitative sandwich enzyme immunoassay utilizing a unique monoclonal antibody directed against an antigenic determinant on the Haptoglobin molecule. The anti-human haptoglobin antibody is used for solid phase immobilization (on the microtiter wells). The same monoclonal anti-human haptoglobin antibody is conjugated to horseradish peroxidase (HRP) and is in the enzyme conjugate solution. The test samples are allowed to react sequentially with the capture monoclonal on the microtiter wells and the enzyme conjugate solution resulting in the Hp molecule to be sandwiched between the solid phase and enzyme-linked antibody.

After two separate 30-minute incubation steps at room temperature with shaking, the wells are rinsed with Wash Buffer to remove unbound Hp protein and unbound labeled antibody respectively. TMB Reagent is added and incubated for 15 minutes with shaking, resulting in the development of a blue color. The color development is stopped with the addition of Stop Solution, changing the color to yellow, and is proportional to the concentration of Hp protein. Absorbance is measured using a spectrophotometer at 450 nm. The absorbance cut-off range for the Hp 2-2 phenotype of Hp is determined by multiplying the absorbance of the Hp 2-2 Control by a pre-determined factor. The absorbance of each sample is compared to the cut-off to determine whether the sample is or is not the Hp 2-2 phenotype.

Test performance. The analytical sensitivity, or the limit of blank of the kit is 0.050, determined by taking the mean of 10 buffer blank determinations plus 2 standard deviations (0.044+2×0.003=0.050). Intra-assay and inter-assay variability (precision) of the kit were determined at two sites by testing 3 human serum samples and one buffer blank. The samples were assayed 8 times using a single lot of reagents over 10 days. Precision data is summarized below.

| | Sample Abs (450 nm) | Intra-assay % CV | | Inter-assay % CV |
|---|---|---|---|---|
| Site #1 | | | | |
| Buffer  n = 8 | 0.044 | 2.4% | n = 80 | 7.5% |
| Hp 1-1  n = 8 | 0.059 | 2.0% | n = 80 | 4.6% |
| Hp 2-1  n = 8 | 1.103 | 2.3% | n = 80 | 2.6% |
| Hp 2-2  n = 8 | 2.376 | 1.2% | n = 80 | 2.9% |
| Site #2 | | | | |
| Buffer  n = 8 | 0.048 | 8.3% | n = 80 | 10.1% |
| Hp 1-1  n = 8 | 0.057 | 6.7% | n = 80 | 8.0% |
| Hp 2-1  n = 8 | 1.243 | 2.8% | n = 80 | 6.8% |
| Hp 2-2  n = 8 | 2.470 | 2.3% | n = 80 | 4.5% |

To determine the limit of detection, two Hp 2-2 samples were diluted from 1:10 to 1:4000 and run in both electrophoresis and in the kit. The two samples were correctly identified as Hp 2-2 down to a dilution of 1:50 by electrophoresis, and down to a dilution of 1:1000 in the kit. Two Hp 1-1 and two Hp 2-1 samples were also diluted from 1:10 through 1:4000 and were also correctly identified as non-Hp 2-2 by the kit at all dilutions tested.

The cut-off of the kit was determined by testing 411 samples of known Hp phenotype, and analyzing the data by using Receiver Operating Characteristic (ROC) plots. The Hp 2-2 cutoff to be used by laboratories with the kit is determined by multiplying the mean Hp 2-2 Positive Control value by an Adjustment Factor of 0.6. The Adjustment Factor accounts for run-to-run as well as day-to-day assay variation.

Interfering substances. Endogenous substances found in blood and exogenous substances (common and prescription drugs) were evaluated for interference in the kit. Six serum samples, two of each Hp phenotype (Hp 1-1, Hp 2-1, Hp 2-2), with Hp EIA absorbance ranging from 0.045 to 2.521, were spiked with potential interferents. As shown below, no appreciable interference was observed for the following substances at the spiked levels tested.

| Endogenous Interferent | |
|---|---|
| Bilirubin | 20 mg/dl (0.2 g/L) |
| Cholesterol | 500 mg/dl (5 g/L) |
| Triglyceride | 2000 mg/ml (20 g/L) |
| BSA | 1500 mg/dL |
| Hemoglobin | 1280 mg/dl (12.8 g/L) |
| Exogenous Interferent | |
| Ascorbic acid (Vitamin C) | 342 umol/L |
| Atorvastatin (Lipitor) | 20 umol/L |
| Niacin | 6500 umol/L |
| Pravastatin | 10 umol/L |
| Warfarin | 32.5 umol/L |
| Acetaminophen | 1324 umol/L |
| Tolbutamide | 2.37 mmol/L |
| Aspirin | 3.62 mmol/L |
| Fenofibrate | 125 umol/L |
| Diphenhydramine | 19.6 umol/L |
| Lisinopril | 0.74 umol/L |
| Motormen | 310 umol/L |

Clinical accuracy. Three studies were undertaken to compare the performance of the kit and the reference methods (polyacrylamide gel electrophoresis or polymerase chain reaction, PCR) in identifying which patients possess the Haptoglobin 2-2 phenotype. Samples consisted of serum and plasma samples from Type I diabetic, Type II diabetic and non-diabetic individuals. 4134 total samples were tested at three sites consisting of the following: Type I diabetics (354 samples, 8.6%); Type II diabetics (3,205 samples, 77.5%); and Non-diabetic individuals (575 samples, 13.9%).

Data were analyzed to determine the diagnostic sensitivity, specificity and agreement between the test method and reference methods. The three clinical studies gave very similar performance parameters when comparing the kit to the reference methods. These results show that the kit can be used to determine Hp 2-2 genotype status in Type I and Type II diabetic patients as well as non-diabetic patients. Thus, the kit is a Sensitive and Specific test for Hp 2-2 genotype.

| | Sensitivity | Specificity | Agreement |
|---|---|---|---|
| Study 1 | 316/317 = 99.7% | 349/350 = 99.7% | 665/667 = 99.7% |
| Study 2 | 1521/1535 = 99.1% | 1548/1570 = 98.6% | 3069/3105 = 98.8% |
| Study 3 | 148/155 = 95.5% | 198/199 = 99.5% | 346/354 = 97.7% |

In addition, in one clinical study the data were further analyzed by preparing and comparing Primary Composite plots and Kaplan-Meier plots from both the test method and the reference method. These plots demonstrated that the kit is comparable to the reference method in assessing cardiovascular risk in diabetics.

The following description provides further operational details on an exemplary kit embodied here.

Haptoglobin (Hp) is a normally occurring acute phase serum protein whose primary physiological role is to scavenge free hemoglobin (Hb), a potent oxidizing agent, from circulation. Free Hb, released during hemolysis of red blood cells, promotes the accumulation of hydroxyl free radicals which can cause oxidative damage to tissues. Hp acts as an antioxidant by first forming complexes with Hb and then being cleared from the circulation by uptake via the CD163 macrophage receptor. Hp is polymorphic in human sand occurs as either one of three phenotypes, Hp 1-1, Hp 2-1 or Hp 2-2. The prevalence of the three phenotypes of Hp is 16% Hp 1-1, 48% Hp 2-1 and 36% Hp 2-2. Substantial evidence supports the pathogenetic role for the Hp 2-2 phenotype. The clearance of the Hb-Hp complex is Hp phenotype dependent. The Hp 2-2 phenotype appears to be an inferior antioxidant compared to the Hp 1-1 phenotype. The Hp 1-1 is also more efficient in preventing heme release from Hp-Hb complexes and in being cleared by the CD 163 macrophage receptor. Finally, recent studies show impaired reverse cholesterol transport in diabetics with Hp 2-2.

The presence of the Hp 2-2 phenotype in diabetic individuals predicts cardiovascular risk. Several longitudinal studies have established that the Hp 2-2 phenotype is an independent risk factor for coronary artery disease, myocardial infarction and death from cardiovascular disease in diabetic individuals. Although the distribution of Hp phenotypes is not different in individuals with or without diabetes 1, the Hp 2-2 phenotype was shown to be a risk factor only in patients with diabetes. This may occur because in a diabetic patient, glycosylation of hemoglobin and the reduction of CD163 receptor in macrophages may contribute to the increase of oxidative stress and tissue damage by hemoglobin-haptoglobin complexes. It has been shown that the oxidation of LDL by glycosylated-hemoglobin is not completely blocked by binding to Hp 2-2 and the impaired removal of the complexes results in their localization in HDL particles. Hb and lipid peroxides associated with HDL were increased and HDL function was impaired in Hp 2-2 diabetic individuals. Individuals with Hp 2-2 diabetes display dysfunctional HDL which increases their risk of cardiovascular disease.

The Test Kit is based on the principle of a solid phase enzyme-linked immunosorbent assay. The assay is a qualitative sandwich enzyme immunoassay utilizing a unique monoclonal antibody directed against an antigenic determinant on the Haptoglobin molecule. This mouse monoclonal anti-human haptoglobin antibody is used for solid phase immobilization (on the microtiter wells). The same monoclonal anti-human haptoglobin antibody is conjugated to horseradish peroxidase (HRP) and is in the enzyme conjugate solution. The test samples are allowed to react sequentially with the capture monoclonal on the microtiter wells and the enzyme conjugate solution resulting in the Hp molecule to be sandwiched between the solid phase and enzyme-linked antibody.

After two separate 30-minute incubation steps at room temperature with shaking, the wells are rinsed with Wash Buffer to remove unbound Hp protein and unbound labeled antibody respectively. TMB Reagent is added and incubated for 15 minutes with shaking, resulting in the development of a blue color. The color development is stopped with the addition of Stop Solution, changing the color to yellow, and is proportional to the concentration of Hp protein. Absorbance is measured using a spectrophotometer at 450 nm. The absorbance cut-off range for the Hp 2-2 phenotype of Hp is determined by multiplying the absorbance of the Hp 2-2 Control by a pre-determined factor. The absorbance of each sample is compared to the cut-off to determine whether the sample is or is not the Hp 2-2 phenotype.

Reagents and Materials Provided:

1. Hp Ab Coated Microwells (96 wells, 1 strip plate, 8×12 well strips)
2. Microtiter wells coated with mouse monoclonal anti-human haptoglobin in sealed pouch with desiccant.
3. Sample Diluent (1×50 ml/bottle, 1 bottle, green cap) (For Sample Dilution Use ONLY). Contains phosphate buffer-BSA solution with preservatives
4. Enzyme Conjugate Concentrate 250×(1×0.250 ml vial, red dot on cap). Contains mouse monoclonal anti-haptoglobin conjugated to horseradish peroxidase
5. Enzyme Conjugate Diluent (1×13 ml vial, red cap) For Enzyme Conjugate Concentrate Dilution ONLY
6. Protein-containing diluent with preservatives
7. 20× Wash Buffer (1×50 ml bottle, clear cap)
8. Phosphate buffer with detergents
9. TMB Reagent (one-step) (1×11 ml vial, brown opaque bottle). Contains one-step TMB solution
10. Stop Solution 1N HCl (1×11 ml vial, clear cap). Contains dilute hydrochloric acid.
11. Positive Control Hp 1-1 (1×0.250 ml vial, white dot on cap). Human serum with preservative.
12. Positive Control Hp 2-1 (1×0.250 ml vial, yellow dot on cap). Human serum with preservative.
13. Positive Control Hp 2-2 (1×0.250 ml vial, green dot on cap). Human serum with preservative.

Materials Required but not Provided:

1. Distilled or deionized water ONLY.
2. Precision pipettes: 5 ul, 10 ul, 100 ul and 1.0 ml and disposable pipette tips
3. Microtiter well reader with a bandwidth of 10 nm or less and an optical density range of 0 to 3 OD or greater at 450 nm wavelength is acceptable.
4. EIA plate shaker capable of shaking microplates at 750 rpm
5. Vortex mixer, or equivalent
6. Absorbent paper Warnings and Precautions:

CAUTION: This kit contains human serum. The human serum tested negative for HBsAg, HIV ½ and HCV by FDA-approved methods. However, no method can completely assure absence of these agents; therefore, all human blood products, including serum and plasma samples, should be considered as potentially infectious. Handling should be as defined by an appropriate biohazard safety guideline or regulation, where it exists.

Avoid contact with 1N HCl. It may cause skin irritation and burns. If contact occurs, wash with copious amounts of water and seek medical attention if irritation persists.

Do not use reagents after expiration date and do not mix or use components from kits with different lot numbers.

Use separate clean tips for different specimens. Do not pipette by mouth.

Do not smoke, eat or drink in areas in which specimens or kit reagents are handled.

Wear disposable gloves while handling specimens and thoroughly wash hands after handling. Replace caps on reagents immediately. Do not switch caps.

Storage and Stability:

Store the unopened kit at 2-8° C. upon receipt and when not in use, until the expiration shown on the kit label. Refer to the package label for the expiration date.

Keep microtiter plate in a sealed bag with desiccant to minimize exposure to damp air.

Any improperly sealed product should be discarded.

The Test Kit is stable until the expiration date on the kit label when stored at 2-8° C. Stability testing at accelerated temperatures suggests that the Test Kit is stable stored at elevated temperatures (25° C.-35° C.) for up to two weeks.

Microtiter strips devices must be stored in proper condition (2-30° C.; until expiration date) to ensure proper function.

Specimen Collection and Preparation

Serum Samples: Whole blood should be collected using standard venipuncture techniques. Invert tube several times to adequately mix the blood. Blood tubes should be stored at room temperature for at least 2 hours, but no more than 5 hours before centrifuging samples at 2,500 rpm for 20 minutes at 40° C. Remove serum supernatant and store at 2-8° C. for up to 48 hours. Store at −20° C. or below, for long term storage.

Plasma Samples: EDTA, heparin, or citrate plasma may be used in the assay.

Avoid hemolytic (red) samples (after centrifugation). Hemolyzed samples have been shown to give inaccurate results.

Specimens should not be repeatedly frozen and thawed prior to testing.

DO NOT store in "frost free" freezers, which may cause occasional thawing. Specimens that have been frozen, and those which are turbid and/or contain particulate matter, must be centrifuged prior to use.

Avoid contact with skin by wearing gloves and proper laboratory attire.

Kit/Reagent Preparation

All reagents should be allowed to reach room temperature (18-25° C.) before use, except the Enzyme Conjugate Concentrate 250× reagent. Always keep Enzyme Conjugate Concentrate reagent at 2-8° C.

Sample Preparation: Patient serum should be diluted 1:10 with Sample Diluent prior to use. Prepare a series of small tubes (i.e. 1.5 ml microcentrifuge tubes) and add 15 nl of serum with 135 nl of Sample Diluent.

Quality Control

Good Laboratory practice recommends the daily use of control materials to validate the reliability of the test device.

If control values do not fall within the established ranges, assay results are invalid.

Kit/Reagent Preparation

Working Conjugate Reagent: To prepare Working Hp Conjugate reagent, dilute the Enzyme Conjugate Concentrate (250×) with the Enzyme Conjugate Diluent. Add 0.004 ml of Enzyme Conjugate Concentrate (250×) to 1.0 ml of Conjugate Diluent. DO NOT REUSE THE WORKING ENZYME CONJUGATE REAGENT. MAKE A FRESH DILUTION BEFORE EACH ASSAY.

Working Wash Buffer: Preparation of 1× Wash Buffer from 20× stock. Add 50 ml of 20× Wash Buffer Stock to 950 ml of deionized water. The Working Wash Buffer is stable at 2-8° C. for 30 days. NOTE: Any crystals that may be present due to high salt concentration must be re-dissolved at room temperature before making the dilution.

Test Procedure

NOTE: Pipetting Recommendations (single and multi-channel): Pipetting of all samples and controls should be completed within 15 minutes. Samples should be diluted 1:10 prior to use. See Sample Reagent preparations. Secure the desired number of coated wells in holder. Dispense 100 µl of Sample Diluent into the A1, B1 well as background control. Dispense 100 µl of each DILUTED (1:10) Positive Control Samples in duplicate, one each into the third through eighth well (C1 to H1). Dispense DILUTED samples into the appropriate wells. Incubate for 30 minutes at room temperature (18-25° C.) on a plate shaker set to approximately 750 rpm. Remove incubation mixture by flicking plate contents into a waste container. Rinse and flick the microtiter wells 5 times with 300 µl Working Wash Buffer. Strike the wells onto absorbent paper or paper towels to remove residual water droplets. Dispense 100 µl of Working Hp Conjugate solution into each well. Incubate for 30 minutes at room temperature (18-25° C.) on a plate shaker set to approximately 750 rpm. Remove incubation mixture by flicking plate contents into a waste container. Rinse and flick the microtiter wells 5 times with 300 µl Working Wash Buffer. Strike the wells onto absorbent paper or paper towels to remove residual water droplets. Dispense 100 µl of TMB solution into each well. Incubate for 15 minutes at room temperature (18-25° C.) on a plate shaker set at about 750 rpm. Stop the reaction by adding 100 µl of Stop Solution to each well. Gently mix for 30 seconds. It is important to make sure that all the blue color changes to yellow color completely. Read absorbance at 450 nm with a microtiter well reader within 15 minutes.

Interpretation of Test Results

Compare the mean absorbance of the Positive Control (PC) samples to the assay ranges supplied with each kit on the Certificate of Analysis. PC Hp 1-1 should fall within the range for Hp 1-1 samples, PC Hp 2-1 should fall within the range of Hp 2-1 samples, and PC Hp 2-2 should fall within the range of Hp 2-2 samples. If any of the PCs do not fall in the appropriate range, the assay needs to be repeated.

The Cutoff for Hp 2-2 samples is calculated by multiplying the Hp 2-2 control O.D. reading with the Cutoff Adjustment Factor indicated in the Certificate of Analysis. For example: Hp 2-2 Cutoff Factor=0.6. Hp 2-2 Control O.D.=2.4. Cutoff for Hp 2-2=2.4×0.6=1.44

In this example, any sample with O.D. readings above 1.44 is an Hp 2-2 phenotype. Any sample with reading below 1.44 is not an Hp 2-2 phenotype.

The above calculation is for demonstration purposes only. Each operator should determine the Hp 2-2 Cutoff Value for each experiment.

The Hp 2-2 Cutoff Adjustment Factors are set by the manufacturer with each lot of kits by running at least 50 samples of each phenotype and determining the optimum sensitivity and specificity using Receiver Operating Characteristics (ROC) plots. Samples whose O.D. reading falls within 10% of a cutoff should be repeated. Samples whose results fall within 10% of the cutoff again should be reported as a borderline Hp 2-2 result.

Limitations of the Procedure

Serum and plasma samples that demonstrate hemolysis should not be used with the Test Kit. Hemolyzed samples have been shown to give inaccurate results.

Do not use this assay to determine Hp 2-2 status in patients with Multiple Myeloma.

Reliable and reproducible results will be obtained when the assay procedure is carried out according to the package insert instructions and with adherence to good laboratory practice.

The results obtained from the use of the Test Kit should be used as an adjunct to other diagnostic procedures and information available to the physician.

The wash procedure is critical. Insufficient washing will result in poor precision and falsely elevated absorbance readings.

Patient samples may contain human anti-mouse antibodies (HAMA) that are capable of giving falsely elevated or depressed results with assays that utilize mouse monoclonal antibodies. This assay has been designed to minimize interference from HAMA-containing specimens. Nevertheless, complete elimination of this interference from all patient specimens cannot be guaranteed.

It is recommended that the wells be read within 15 minutes following the addition of Stop Solution.

Expected Values

The Test Kit is a qualitative assay, which identifies the Hp 2-2 phenotype in human serum or plasma as present or absent. Confirmation of the Hp 2-2 phenotype, as well as questionable results should be confirmed by using an alternate method, preferably gel electrophoresis.

Test Performance

Precision. Intra-assay and inter-assay variability (precision) of the HAPTOCHEK™ Test Kit were determined at two sites by testing 3 human serum samples and one buffer blank. The samples were assayed 8 times using a single lot of reagents over 10 days. Precision data is provided above.

What is claimed is:

1. An isolated anti-haptoglobin monoclonal antibody, comprising at least one light chain variable region and at least one heavy chain variable region,
    said light chain variable region comprising:
        the complementarity determining region light chain (CDRL) 1 comprising amino acid sequence SEQ ID NO:3;
        a CDRL2 comprising amino acid sequence SEQ ID NO:4; and
        a CDRL3 comprising amino acid sequence of SEQ ID NO:5, and
    said heavy chain variable region comprising:
        a complementarity determining region heavy chain (CDRH) 1 comprising amino acid sequence SEQ ID NO:8;
        a CDRH2 comprising amino acid sequence SEQ ID NO:9; and
        a CDRH3 comprising amino acid sequence SEQ ID NO:10.

2. The isolated anti-haptoglobin monoclonal antibody of claim 1, comprising a light chain variable region amino acid sequence of SEQ ID NO:2.

3. The isolated anti-haptoglobin monoclonal antibody of claim 1, comprising a heavy chain variable region amino acid sequence of SEQ ID NO:7.

4. The isolated anti-haptoglobin monoclonal antibody of claim 1, comprising a light chain variable region of SEQ ID NO:2 and a heavy chain variable amino acid sequence of SEQ ID NO:7.

5. The isolated anti-haptoglobin monoclonal antibody of claim 1, wherein said antibody light or heavy chain variable region is at least one of chimerized, humanized, or CDR-grafted.

6. The isolated anti-haptoglobin monoclonal antibody of claim 5, further comprising at least one compound or polypeptide selected from a detectable label or reporter.

7. The isolated anti-haptoglobin monoclonal antibody of claim 6 wherein the detectable label is an enzyme.

8. The isolated anti-haptoglobin monoclonal antibody of claim 7 wherein the enzyme is horseradish peroxidase or alkaline phosphatase.

9. The isolated anti-haptoglobin monoclonal antibody of claim 1, having a binding affinity in decreasing order to haptoglobin isoforms Hp2-2; Hp2-1; and Hp 1-1.

10. The isolated monoclonal anti-haptoglobin monoclonal antibody of claim 1 wherein the antibody is produced by the murine hybridoma deposited with the ATCC having a patent deposit designation PTA-9815.

11. A nucleotide sequence encoding the light chain variable region of the isolated anti-haptoglobin monoclonal antibody of claim 1, wherein the nucleotide sequence is SEQ ID NO: 1.

12. A nucleotide sequence encoding the heavy chain variable region of the isolated anti-haptoglobin monoclonal antibody of claim 1, wherein the nucleotide sequence is SEQ ID NO: 6.

* * * * *